US009468598B2

(12) United States Patent
Dietrich et al.

(10) Patent No.: US 9,468,598 B2
(45) Date of Patent: *Oct. 18, 2016

(54) ORAL DOSAGE FORM CONTAINING A PDE 4 INHIBITOR AS AN ACTIVE INGREDIENT AND POLYVINYLPYRROLIDON AS EXCIPIENT

(71) Applicant: AstraZeneca AB, Mölndal (SE)

(72) Inventors: Rango Dietrich, Constance (DE); Klaus Eistetter, Constance (DE); Hartmut Ney, Constance (DE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/874,065

(22) Filed: Apr. 30, 2013

(65) Prior Publication Data

US 2013/0345265 A1 Dec. 26, 2013

Related U.S. Application Data

(63) Continuation of application No. 13/008,842, filed on Jan. 18, 2011, now Pat. No. 8,431,154, which is a continuation of application No. 10/505,138, filed as application No. PCT/EP03/01650 on Feb. 19, 2003, now Pat. No. 7,951,397.

(30) Foreign Application Priority Data

Feb. 20, 2002 (DE) .................................. 102 07 160
Feb. 20, 2002 (EP) ..................................... 02003811

(51) Int. Cl.
*A61K 9/20* (2006.01)
*A61K 9/00* (2006.01)
*A61K 31/166* (2006.01)
*A61K 31/44* (2006.01)

(52) U.S. Cl.
CPC ........... *A61K 9/0002* (2013.01); *A61K 9/2027* (2013.01); *A61K 31/166* (2013.01); *A61K 31/44* (2013.01)
USPC ........................................................ 424/464

(58) Field of Classification Search
CPC .................................................. A61K 31/166
See application file for complete search history.

(56) References Cited

U.S. PATENT DOCUMENTS

| | | |
|---|---|---|
| 3,065,142 A | 11/1962 | Antonides |
| 4,006,227 A | 2/1977 | Gallegos et al. |
| 4,024,240 A | 5/1977 | Thakkar |

(Continued)

FOREIGN PATENT DOCUMENTS

| | | |
|---|---|---|
| CA | 2065364 | 10/1990 |
| CA | 2016141 | 11/1990 |

(Continued)

OTHER PUBLICATIONS

Academic book—*Applied Pharmacy Farmacja Stosowana Fiebig Janicki*, 2001, pp. 267-268.

(Continued)

*Primary Examiner* — Paul Dickinson
(74) *Attorney, Agent, or Firm* — Fish & Richardson P.C.

(57) ABSTRACT

Dosage forms for oral administration of a PDE 4 inhibitor whose solubility is slight are described. They contain PVP as binder.

41 Claims, 1 Drawing Sheet

(56) References Cited

U.S. PATENT DOCUMENTS

| | | | |
|---|---|---|---|
| 4,343,804 A | 8/1982 | Munson et al. |
| 4,349,563 A | 9/1982 | Gilbert et al. |
| 4,450,164 A | 5/1984 | Bristol et al. |
| 4,464,372 A | 8/1984 | Bristol et al. |
| 4,563,455 A | 1/1986 | Ueda et al. |
| 4,621,084 A | 11/1986 | Takaya et al. |
| 4,686,227 A | 8/1987 | Ueda et al. |
| 4,725,601 A | 2/1988 | Ueda et al. |
| 4,753,945 A | 6/1988 | Gilbard et al. |
| 4,769,384 A | 9/1988 | Kise et al. |
| 4,782,055 A | 11/1988 | Ueda et al. |
| 4,791,117 A | 12/1988 | Press |
| 4,806,550 A | 2/1989 | Ife et al. |
| 4,831,041 A | 5/1989 | Shiokawa et al. |
| 4,833,149 A | 5/1989 | Press |
| 4,839,353 A | 6/1989 | Hosoi et al. |
| 4,900,775 A | 2/1990 | Smith et al. |
| 4,920,129 A | 4/1990 | Shiokawa et al. |
| 5,006,595 A | 4/1991 | Smith et al. |
| 5,011,843 A | 4/1991 | Shell |
| 5,041,442 A | 8/1991 | Romero et al. |
| 5,051,508 A | 9/1991 | Brown et al. |
| 5,089,504 A | 2/1992 | Ife et al. |
| 5,102,892 A | 4/1992 | Geiss et al. |
| 5,112,834 A | 5/1992 | Senn-Bilfinger |
| 5,188,838 A | 2/1993 | Deleuil et al. |
| 5,200,417 A | 4/1993 | Brown et al. |
| 5,215,999 A | 6/1993 | Uchida et al. |
| 5,252,580 A | 10/1993 | Takahashi et al. |
| 5,262,171 A | 11/1993 | Login et al. |
| 5,286,494 A | 2/1994 | Fechner et al. |
| 5,320,848 A | 6/1994 | Geyer et al. |
| 5,326,879 A | 7/1994 | Takahashi et al. |
| 5,340,827 A | 8/1994 | Beeley et al. |
| 5,380,532 A | 1/1995 | Deleuil et al. |
| 5,409,943 A | 4/1995 | Ife et al. |
| 5,429,824 A | 7/1995 | June |
| 5,439,917 A | 8/1995 | Briving et al. |
| 5,449,676 A | 9/1995 | Amschler et al. |
| 5,534,515 A | 7/1996 | Grundler |
| 5,559,110 A * | 9/1996 | Aungst ............ 514/218 |
| 5,594,013 A | 1/1997 | Trigger |
| 5,665,730 A | 9/1997 | Senn-Bilfinger et al. |
| 5,677,302 A | 10/1997 | Karimian et al. |
| 5,686,458 A | 11/1997 | Lee et al. |
| 5,698,711 A | 12/1997 | Palfreyman |
| 5,712,298 A | 1/1998 | Amschler |
| 5,719,161 A | 2/1998 | Rainer |
| 5,762,953 A | 6/1998 | Venkateshwaran |
| 5,824,687 A | 10/1998 | Senn-Bilfinger |
| 5,891,904 A | 4/1999 | Stief et al. |
| 5,914,334 A | 6/1999 | Charu |
| 5,935,978 A | 8/1999 | Fenton et al. |
| 5,972,381 A | 10/1999 | Sangekar et al. |
| 5,972,927 A | 10/1999 | Pascal et al. |
| 6,114,537 A | 9/2000 | Karimian et al. |
| 6,124,313 A | 9/2000 | Grundler et al. |
| 6,132,770 A | 10/2000 | Lundberg |
| 6,160,119 A | 12/2000 | Senn-Bilfinger |
| 6,174,878 B1 | 1/2001 | Gamache et al. |
| 6,218,400 B1 | 4/2001 | Daugan et al. |
| 6,231,885 B1 | 5/2001 | Carrara |
| 6,255,326 B1 | 7/2001 | Ashton |
| 6,258,833 B1 | 7/2001 | Martins et al. |
| 6,265,415 B1 | 7/2001 | Amin et al. |
| 6,270,807 B1 | 8/2001 | Danielson et al. |
| 6,288,118 B1 | 9/2001 | Nieman et al. |
| 6,313,136 B1 | 11/2001 | Amin et al. |
| 6,313,137 B1 | 11/2001 | Amin et al. |
| 6,328,993 B1 | 12/2001 | Linder et al. |
| 6,348,602 B1 | 2/2002 | Fowler et al. |
| 6,375,968 B1 | 4/2002 | Quong |
| 6,379,682 B1 | 4/2002 | Tchinnis et al. |
| 6,383,510 B1 | 5/2002 | Linder et al. |
| 6,384,048 B1 | 5/2002 | Senn-Bilfinger |
| 6,417,190 B1 | 7/2002 | Hoffmann et al. |
| 6,432,451 B1 | 8/2002 | Lee et al. |
| 6,436,953 B1 | 8/2002 | Senn-Bilfinger |
| 6,436,970 B1 | 8/2002 | Hafner et al. |
| 6,448,274 B2 | 9/2002 | Friesen et al. |
| 6,498,173 B1 | 12/2002 | Kilian |
| 6,503,923 B1 | 1/2003 | Senn-Bilfinger |
| 6,531,493 B1 | 3/2003 | Kley et al. |
| 6,537,983 B1 | 3/2003 | Biggadike et al. |
| 6,555,583 B2 | 4/2003 | Nieman et al. |
| 6,579,884 B1 | 6/2003 | Amin et al. |
| 6,613,775 B1 | 9/2003 | Amin et al. |
| 6,624,181 B1 | 9/2003 | Killian et al. |
| 6,630,161 B1 | 10/2003 | Leesman |
| 6,670,394 B1 | 12/2003 | Christensen et al. |
| 6,677,362 B1 | 1/2004 | Ghebre et al. |
| 6,743,443 B1 | 6/2004 | Furitsu et al. |
| 6,767,557 B2 | 7/2004 | Ulrich et al. |
| 6,822,114 B1 | 11/2004 | Williams et al. |
| 6,872,382 B1 | 3/2005 | Gamache et al. |
| 6,897,229 B2 | 5/2005 | Kilian |
| 7,056,936 B2 | 6/2006 | Killian et al. |
| 7,076,437 B1 | 7/2006 | Levy |
| 7,147,869 B2 | 12/2006 | Dietrich et al. |
| 7,175,854 B2 | 2/2007 | Dietrich et al. |
| 7,182,958 B1 | 2/2007 | Oren et al. |
| 7,357,943 B2 | 4/2008 | Linder et al. |
| 7,393,860 B1 | 7/2008 | Senn-Bilfinger |
| D580,547 S | 11/2008 | Lolis et al. |
| 7,470,791 B2 | 12/2008 | Kohl et al. |
| 7,745,646 B2 | 6/2010 | Govek et al. |
| 7,785,630 B2 | 8/2010 | Dietrich et al. |
| 7,790,198 B2 | 9/2010 | Dietrich et al. |
| 7,794,752 B1 | 9/2010 | Dietrich et al. |
| 7,927,623 B2 | 4/2011 | Sugimoto et al. |
| 7,951,397 B2 | 5/2011 | Dietrich et al. |
| 7,951,398 B2 | 5/2011 | Dietrich et al. |
| 8,431,154 B2 | 4/2013 | Dietrich et al. |
| 8,536,206 B2 | 9/2013 | Kohl et al. |
| 8,604,064 B2 | 12/2013 | Kohl et al. |
| 8,618,142 B2 | 12/2013 | Kohl et al. |
| 8,663,694 B2 | 3/2014 | Bruck-Scheffler et al. |
| 9,205,044 B2 | 12/2015 | Linder et al. |
| 2001/0044409 A1 | 11/2001 | Ghebre et al. |
| 2002/0002191 A1 | 1/2002 | Friesen |
| 2002/0006418 A1 | 1/2002 | Kung et al. |
| 2002/0086039 A1 | 7/2002 | Lee et al. |
| 2002/0193393 A1 | 12/2002 | Pairet et al. |
| 2003/0018071 A1 | 1/2003 | Rennard et al. |
| 2003/0092706 A1 | 5/2003 | Barsig |
| 2003/0099700 A1 | 5/2003 | Faham et al. |
| 2003/0187006 A1 | 10/2003 | Hagan |
| 2003/0195233 A1 | 10/2003 | Magee |
| 2003/0207845 A1 | 11/2003 | Keating et al. |
| 2003/0212112 A1 | 11/2003 | Murdoch et al. |
| 2003/0215498 A1 | 11/2003 | Harland |
| 2004/0024007 A1 | 2/2004 | Pairet et al. |
| 2004/0058896 A1 | 3/2004 | Dietrich et al. |
| 2004/0058950 A1 | 3/2004 | Meade et al. |
| 2004/0101558 A1 | 5/2004 | Dietrich et al. |
| 2004/0151722 A1 | 8/2004 | Banerjee et al. |
| 2004/0241235 A1 | 12/2004 | Lebon et al. |
| 2005/0159492 A1 | 7/2005 | Dietrich et al. |
| 2006/0004061 A1 | 1/2006 | Kohl et al. |
| 2006/0069155 A1 | 3/2006 | Edelson |
| 2006/0084684 A1 | 4/2006 | Bolle et al. |
| 2006/0084685 A1 | 4/2006 | Koenen et al. |
| 2006/0105038 A1 | 5/2006 | Lai et al. |
| 2006/0142308 A1 | 6/2006 | Kolassa et al. |
| 2006/0147382 A1 | 7/2006 | Bundschuh et al. |
| 2006/0159758 A1 | 7/2006 | Gandhi et al. |
| 2006/0198889 A1 | 9/2006 | Sandhu et al. |
| 2006/0199865 A1 | 9/2006 | Beume et al. |
| 2006/0228410 A1 | 10/2006 | Dumont et al. |
| 2006/0269600 A1 | 11/2006 | Dietrich |
| 2006/0293343 A1 | 12/2006 | Naganuma et al. |
| 2007/0111995 A1 | 5/2007 | Allen |
| 2007/0122474 A1 | 5/2007 | Dietrich |
| 2007/0134729 A1 | 6/2007 | Christensen et al. |

(56) References Cited

U.S. PATENT DOCUMENTS

| | | |
|---|---|---|
| 2007/0254928 A1 | 11/2007 | Wollin et al. |
| 2008/0193544 A1 | 8/2008 | Bruck-Scheffler et al. |
| 2008/0280958 A1 | 11/2008 | Bolle et al. |
| 2009/0171096 A1 | 7/2009 | Kohl et al. |
| 2010/0310477 A1 | 12/2010 | Pairet et al. |
| 2011/0060016 A1 | 3/2011 | Dietrich et al. |
| 2011/0212182 A1 | 9/2011 | Lebon et al. |
| 2011/0251244 A1 | 10/2011 | Dietrich et al. |
| 2011/0313005 A1 | 12/2011 | Bolle et al. |
| 2012/0052122 A1 | 3/2012 | Bredenbroeker |
| 2012/0289552 A1 | 11/2012 | Dumas et al. |
| 2013/0131123 A1 | 5/2013 | Dietrich et al. |
| 2013/0252976 A1 | 9/2013 | Carra et al. |
| 2014/0031396 A1 | 1/2014 | Dietrich et al. |
| 2014/0031397 A1 | 1/2014 | Dietrich et al. |
| 2014/0155315 A1 | 6/2014 | Zecri et al. |
| 2015/0290178 A1 | 10/2015 | Dietrich et al. |
| 2015/0290179 A1 | 10/2015 | Dietrich et al. |
| 2015/0290180 A1 | 10/2015 | Dietrich et al. |

FOREIGN PATENT DOCUMENTS

| | | |
|---|---|---|
| CA | 2497176 | 3/2004 |
| CN | 1126468 | 11/2003 |
| CN | 1189832 | 2/2005 |
| DE | 3011490 | 3/1981 |
| DE | 3622036 | 1/1987 |
| DE | 3917232 | 11/1990 |
| DE | 3943385 | 7/1991 |
| DE | 69101493 | 8/1994 |
| DE | 10061137 | 6/2002 |
| DE | 19925710 | 10/2002 |
| EP | 33094 | 8/1981 |
| EP | 68378 | 1/1983 |
| EP | 120589 | 10/1984 |
| EP | 125756 | 11/1984 |
| EP | 165545 | 12/1985 |
| EP | 228006 | 7/1987 |
| EP | 261912 | 3/1988 |
| EP | 264883 | 4/1988 |
| EP | 266890 | 5/1988 |
| EP | 268989 | 6/1988 |
| EP | 308917 | 3/1989 |
| EP | 163965 | 11/1989 |
| EP | 368158 | 5/1990 |
| EP | 120352 | 6/1990 |
| EP | 438359 | 7/1991 |
| EP | 399267 | 12/1991 |
| EP | 204285 | 1/1992 |
| EP | 259174 | 3/1992 |
| EP | 307078 | 8/1992 |
| EP | 509974 | 10/1992 |
| EP | 510562 | 10/1992 |
| EP | 330485 | 5/1993 |
| EP | 563024 | 9/1993 |
| EP | 387821 | 8/1994 |
| EP | 393926 | 9/1994 |
| EP | 617612 | 10/1994 |
| EP | 0719561 A1 | 7/1996 |
| EP | 537532 | 11/1996 |
| EP | 535529 | 7/1997 |
| EP | 1118615 | 7/2001 |
| EP | 1161950 | 12/2001 |
| EP | 1187601 | 3/2002 |
| EP | 1105390 | 6/2003 |
| EP | 1199074 | 4/2004 |
| EP | 1366760 | 9/2005 |
| EP | 1120120 | 4/2009 |
| EP | 1478399 | 3/2012 |
| ES | 2176252 | 12/2002 |
| JP | 61205208 | 9/1986 |
| JP | S61205208 | 9/1986 |
| JP | H249720 | 2/1990 |
| JP | 2270873 | 11/1990 |
| JP | 2049720 | 12/1990 |
| JP | 3284622 | 12/1991 |
| JP | 3284686 | 12/1991 |
| JP | 4212359 | 8/1992 |
| JP | 5271070 | 10/1993 |
| JP | 3031280 | 11/1996 |
| JP | 8-512041 | 12/1996 |
| JP | 9059152 | 3/1997 |
| JP | 11152224 | 6/1999 |
| JP | 2000516633 | 12/2000 |
| JP | 20086502 | 7/2009 |
| KR | 2000-0029011 | 5/2000 |
| KR | 00331255 | 10/2002 |
| PL | 178314 | 1/1995 |
| WO | 8900570 | 1/1989 |
| WO | 8908127 | 9/1989 |
| WO | WO 90/12789 | 11/1990 |
| WO | 9114677 | 10/1991 |
| WO | 9117164 | 11/1991 |
| WO | 9118887 | 12/1991 |
| WO | 9206979 | 4/1992 |
| WO | WO9206963 | 4/1992 |
| WO | 9212961 | 8/1992 |
| WO | 9212969 | 8/1992 |
| WO | WO 92/19602 | 11/1992 |
| WO | 9221328 | 12/1992 |
| WO | 9308190 | 4/1993 |
| WO | WO9315044 | 5/1993 |
| WO | WO9315045 | 5/1993 |
| WO | 9312090 | 6/1993 |
| WO | 9315055 | 8/1993 |
| WO | 9315056 | 8/1993 |
| WO | 9315071 | 8/1993 |
| WO | WO9315044 | 8/1993 |
| WO | WO9315045 | 8/1993 |
| WO | 9325517 | 12/1993 |
| WO | 9402465 | 2/1994 |
| WO | 9414795 | 7/1994 |
| WO | 9424130 | 10/1994 |
| WO | 9501338 | 1/1995 |
| WO | 9527714 | 10/1995 |
| WO | 9617830 | 6/1996 |
| WO | 9725030 | 7/1997 |
| WO | 9736905 | 10/1997 |
| WO | WO9744036 | 11/1997 |
| WO | 9807400 | 2/1998 |
| WO | WO9809961 | 3/1998 |
| WO | 9820858 | 5/1998 |
| WO | 9835683 | 8/1998 |
| WO | 9837080 | 8/1998 |
| WO | 9842707 | 10/1998 |
| WO | WO 98/49169 | 11/1998 |
| WO | 9854188 | 12/1998 |
| WO | WO9809961 | 12/1998 |
| WO | 9929299 | 6/1999 |
| WO | 9955705 | 11/1999 |
| WO | 9955706 | 11/1999 |
| WO | 9963940 | 12/1999 |
| WO | WO0006121 | 2/2000 |
| WO | 0010999 | 3/2000 |
| WO | 0012501 | 3/2000 |
| WO | 0017200 | 3/2000 |
| WO | 0018388 | 4/2000 |
| WO | 0026217 | 5/2000 |
| WO | 0011000 | 6/2000 |
| WO | 0050011 | 8/2000 |
| WO | 0035428 | 9/2000 |
| WO | 0051598 | 9/2000 |
| WO | 0053182 | 9/2000 |
| WO | 0063211 | 10/2000 |
| WO | WO0006121 | 10/2000 |
| WO | 0066123 | 11/2000 |
| WO | 0074654 | 12/2000 |
| WO | 0108686 | 2/2001 |
| WO | 0115678 | 3/2001 |
| WO | 0132165 | 5/2001 |
| WO | 0146136 | 6/2001 |
| WO | 0157025 | 8/2001 |
| WO | 0160358 | 8/2001 |
| WO | 0190076 | 11/2001 |

(56) References Cited

FOREIGN PATENT DOCUMENTS

| | | |
|---|---|---|
| WO | 0209689 | 2/2002 |
| WO | 0238155 | 5/2002 |
| WO | 0245693 | 6/2002 |
| WO | 02072072 | 12/2002 |
| WO | WO 02/096423 | 12/2002 |
| WO | 03039552 | 5/2003 |
| WO | 03002593 | 8/2003 |
| WO | 03070279 | 8/2003 |
| WO | 03097050 | 11/2003 |
| WO | 03099278 | 12/2003 |
| WO | 03099334 | 12/2003 |
| WO | 03105902 | 12/2003 |
| WO | 2004017974 | 3/2004 |
| WO | 2004019944 | 3/2004 |
| WO | 2004033430 | 4/2004 |
| WO | 2004052345 | 6/2004 |
| WO | 2004066974 | 8/2004 |
| WO | 2004080967 | 9/2004 |
| WO | 2004103407 | 12/2004 |
| WO | 2005011602 | 2/2005 |
| WO | 2005013944 | 2/2005 |
| WO | 2005020961 | 3/2005 |
| WO | 2005026095 | 3/2005 |
| WO | 2005034871 | 4/2005 |
| WO | 2005041864 | 5/2005 |
| WO | 20060097456 | 9/2006 |
| WO | 2008006050 | 1/2008 |
| WO | WO 2012/154563 | 11/2012 |

OTHER PUBLICATIONS

Ammar et al., "Improvement of the biological performance of oral anticoagulant drugs," 1997, Pharmazie, 52:627-631.
Anonym, "Masking the taste of fast-disintegrating tablets," *Inn Pharm Techn*, 2004, 4:109-111.
Antoni et al., "Synthesis of [18F] Labelled Roflumilast Using Difluoro [18F] Bromomethane as Alkylating Agent," *Synthesis and Applications of Isotopically Labeled Compounds*, 2000, 7:375-376.
Assmann, "Subgroup analysis and other (mis) uses of baseline data in 355:1064-69 clinical trials," *Lancet*, 2000, 355:1064-69.
Baraniuk et al., "Inhibition of Phosphodiesterase 4 in Allergic Rhinitis," Review of Schmidt et al., *J Allergy Clin Immunol*, 2001, 108:530-536, Clinical Trials Report, pp. 191-193.
Barnes, "Emerging pharmacotherapies for COPD," *Chest*, 2008, 134:1278-86.
Barsig et al., "Protection by the Phosphodiesterase-4 Inhibitor Roflumilast of Mice Against Collagen-induced Arthritis," 2001, Poster Presentation, 1 page.
Barsig et al., "The Novel Phosphodiesterase-4 Inhibitor Roflumilast Suppresses TNF-a Production and in Combination with Methotrexate Efficiently Protects Mice Against Collagen-induced Arthritis," Arthritis and Rheumatic Diseases, 2001, Poster Presentation, 1 page.
Barsig et al., "The Novel Phosphodiesterase-4 Inhibitor Roflumilast Suppresses TNF-a Production and Efficiently Protects Mice Against Collagen-Induced Arthritis Alone and in Combination with Methotrexate", *Arthritis and Rheumatic Diseases*, 2001, 44(9):Suppl. S367, Abstract.
Bateman et al., "Efficacy of roflumilast in patients with a history of frequent exacerbations: pooled data from pivotal 12-month studies," Poster, ERS Barcelona, Sep. 2010, 1 page.
Bauer et al. , "Lehrbuch der Pharmazeutischen Technologie," 2003, p. 56.
Beers, *Merck Manual of Diagnosis and Therapy*, 17th Edition, 1999, pp. 568-569.
Bethke et al., "Smoking Has No Effect on the Pharmacokinetics of Roflumilast—a New, Orally Active, Selective PDE4 Inhibitor," Eur Respir J., 2001, Poster Presentation, 1 page.
Bethke et al., "Roflumilast, a New, Orally Active, Selective PDE4 Inhibitor, Does Not Interact with Inhaled Budesonide," Eur Respir J, 2001, Poster Presentation, 1 page.

Bethke et al., "Roflumilast, a new, orally active, selective PDE4 inhibitor, does not interact with inhaled budesonide," *Eur Respir J*, 2001, 18:Suppl. 33, 156s, Abstract.
Bethke et al., "Smoking has no effect on the pharmacokinetics of roflumilast, a new, orally active, selective PDE4 inhibitor," *Eur Respir J*, 2001, 18:Suppl. 33, 156s, Abstract.
Bethke et al., "The New PDE4 Inhibitor Roflumilast Does Not Influence Cardiovascular Function," *Am J Respir Crit Care Med*, 2001, 163:A431, Abstract.
Boehmer et al., "Effects of the Dual Pathway Inhibitor Cimetidine on the Pharmacokinetics of Roflumilast and Roflumilast N-oxide," VKliPha 2007 Poster, 2007, 1 page.
Boswell et al., "Are phosphodiesterase 4 inhibitors just more theophylline?," *J Allergy Clin Immunol*, 2006, 117:1237-43.
Bredenbroker et al., "Safety of Once-Daily Roflumilast, a New, Orally Active, Selective Phosphodiesterase 4 Inhibitor, in Patients with COPD," May 2002, poster, 1 page.
Bredenbroker et al., "Safety of Once-Daily Roflumilast, a New, Orally Active, Selective Phosphodiesterase 4 Inhibitor, in Patients with COPD," *Am J Respir Crit Care Med*, May 2002, 165, A595.
Brusasco et al., "Health outcomes following treatment for six months with once daily tiotropium compared with twice daily salmeterol in patients with COPD," *Thorax*, 2003, 58:399-404.
Bühler, *Kollidon: Polyvinylpyrrolidone for the pharmaceutical industry*, 2nd ed., BASF, 1995, pp. 1-287.
Bühler, *Kollidon: Polyvinylpyrrolidone for the pharmaceutical industry*, 4th ed., BASF, 1998, 14 pages.
Bundschuh et al., "Antiinflammatory and Immunomodulatory Potential of Roflumilast, a Novel PDE4 Inhibitor," *Am J Respir Crit Care Med*, 2001, vol. 163, A431, Abstract.
Bundschuh et al., "In vitro and in vivo anti-inflammatory activity of the novel PDE4 inhibitor roflumilast," *Eur Respir J*, 2001, 18:Suppl. 33, 35s, Abstract.
Bundschuh et al., "In Vitro and In Vivo Anti-Inflammatory Activity of the Novel PDE4 Inhibitor Roflumilast," Eur Respir J., 2001, Poster Presentation, 1 page.
Bundschuh et al., "In Vivo Efficacy in Airway Disease Models of Roflumilast. A Novel Orally Active PDE4 Inhibitor", *The Journal of Pharmacology and Experimental Therapeutics*, 2001, 297(1), The American Society for Pharmacology and Experimental Therapeutics, pp. 280-290.
Burge et al., "Randomized, double blind, placebo controlled study of fluticasone propionate in patients with moderate to severe chronic obstructive pulmonary disease: the ISOLDE trial," *BMJ*, 2000, 320:1297-1303.
Calverley et al., "Effect of 1-year treatment with roflumilast in severe chronic obstructive pulmonary disease," *Am. J. Respir. Crit. Care Med.*, 2007, 176:154-161.
Calverley et al., "Maintenance therapy with budesonide and formoterol in chronic obstructive pulmonary disease," 2003, *Eur. Respir. J.*, 22:912-919.
Calverley et al., "Salmeterol and fluticasone propionate and survival in chronic obstructive pulmonary disease," *NEJM*, 2007, 356:8 pages.
Calverley and Walker, "Chronic obstructive pulmonary disease," 2003, *Lancet*, 632:1053-1061.
Calverley et al., "One-year treatment with mometasone furoate in chronic obstructive pulmonary disease," *Resp. Res.*, 2008, 9:11 pages.
Calverley et al., "Combined salmeterol and fluticasone in the treatment of chronic obstructive pulmonary disease: a randomized controlled trial," *Lancet*, 2003, 361:449-56.
Calverley et al., "Defining patient populations in COPD: experience with roflumilast," COPD7 Birmingham, 2010, 1 page.
Calverley et al., "Effect of roflumilast on lung function," ATS 2006 Presentation, 2006, 12 pages.
Calverley et al., "Roflumilast in symptomatic chronic obstructive pulmonary disease: two randomized clinical trials," *Lancet*, 2009, 374:685-94.
Calverley et al., "Roflumilast in symptomatic chronic obstructive pulmonary disease: two randomized clinical trials," *Lancet*, 2009, 374:685-94, Supplementary Web Appendix Content.

(56) References Cited

OTHER PUBLICATIONS

Casas et al, "C-reactive protein and coronary heart disease: a critical review," *J Intern Med*, 2008, 264: 295-314.
Celli and MacNee, "Standards for the diagnosis and treatment of patients with COPD: A summary of the ATS/ERS position paper," *Eur Respir J*, 2004, 23:932-46.
Chen at al., "Long-acting bronchodilator therapy for the treatment of chronic obstructive pulmonary disease," *Ann Pharmacother*, 2008, 42:1832-42.
Chiou and Riegelman, "Pharmaceutical applications of solid dispersion systems," *J. Pharm. Sci.*, 1971, 60:1281-1302.
Chinese Office Action in CN application No. 03804230.4, dated Mar. 29, 2009, 11 pages.
Cocci et al., "Urinary desmosine excretion is inversely correlated with the extent of emphysema in patients with chronic obstructive pulmonary disease," *Int J Biochem Cell Biol*, 2002, 36(6):594-604.
Cook et al., "Process Development of the PDE IV Inhibitor 3-(Cyclopentyloxy)-N-(3,5-dichloropyrid-4-yl)-4-methoxybenzamide," *Organic Process Research & Development*, 1998, 2:157-168.
David et al., "Influence of Food Intake on the Pharmacokinetics of Roflumilast, a New, Orally Active, Selective PDE4 Inhibitor", *Eur Respir J*, 2001, Poster Presentation, 1 page.
David et al., "Influence of food intake on the pharmacokinetics of roflumilast, a new, orally active, selective PDE4 inhibitor", *Eur Respir J*, 2001, 18:Suppl. 33, 42s, Abstract.
Declaration of Dirk Bredenbroeker under Rule 1.132 dated Aug. 17, 2012 in U.S. Appl. No. 11/501,836, filed Aug. 10, 2006, 7 pages.
Declaration of Hermann Tenor under Rule 1.132 dated Aug. 16, 2012 in U.S. Appl. No. 11/501,836, filed Aug. 10, 2006, 9 pages.
Declaration of Hermann Tenor under Rule 1.132 date Nov. 9, 2012 in U.S. Appl. No. 12/876,996, filed Sep. 7, 2010, 3 pages.
Declaration of Walter Palosch under Rule 1.132 dated Mar. 13, 2013 in U.S. Appl. No. 13/547,945, filed Jul. 12, 2012, 4 pages.
Declaration of Hartmut Ney under Rule 1.132 dated Apr. 19, 2007 in U.S. Appl. No. 10/505,138, filed Aug. 19, 2004, 25 pages.
Declaration of Karl Zech under Rule 1.132 dated Jan. 24, 2013 in U.S. Appl. No. 12/876,996, filed Sep. 7, 2010, 4 pages.
Definition: "Solution, colloidal," In: *Hawleys Chemical Condensed Dictionary*, 14th edition, 2002, 1 page.
deMey et al., "Repeated-dose Co-administration of Roflumilast and Formoterol Does not Alter the Pharmacokinetics of Either Drug," ATS 2006 Poster, 2006, 1 page.
deMey et al., "Roflumilast Does not Potentiate Tachycardia Associated with Formoterol," ATS 2006 Poster, 2006, 1 page.
Donaldson et al., "Relationship between exacerbation frequency and lung function decline in chronic obstructive pulmonary disease," *Thorax*, 2002, 57:847-52.
Drugs in R and D-ADIS R&D Profile ,"Roflumilast," 2004, 5(3):176-181.
Ecuador Office Action issued in EC application No. SP-045238, dated Jul. 31, 2008, 3 pages.
Eakin et al., "Validation of a new dyspnea measure: The UCSD shortness of breath questionnaire," *Chest*, 1998, 113:619-24.
Engelstatter, "Roflumilast, an oral, once-daily phosphodiesterase 4 (PDE4) inhibitor, does not exhibit bronchodilatory activity," *Ann Allergy Asthma Immunol*, 2005, 94:169 (abstract).
European Office Action issued in EP application No. 03704652.1, dated Nov. 19, 2010, in corresponding EP case citing EP1161950A1, 6 pages.
Exhibit B-5—*Handbook of Pharmaceutical Excipients*, 2nd Ed, Wade and Weller Eds., 1994, 4 pages.
Exhibit B-6—"Release controlled Oral Preparation," Sep. 2002, 3 pages.
Fabbri et al., "Roflumilast in moderate-to-severe chronic obstructive pulmonary disease treated with long-acting bronchodilators: two randomized clinical trials," *Lancet*, 2009, 374:695-703.
Fabbri et al., "Roflumilast in moderate-to-severe chronic obstructive pulmonary disease treated with long-acting bronchodilators: two randomized clinical trials," 2009, Web Appendix, 28 pages.
Fabbri et al, "Effect of Roflumilast on Exacerbations: a 1-year Study in Patients with Severe to Very Severe COPD ," ATS 2006 Poster, 2006, 1 page.
Facius et al., "Modelling and simulation based techniques to support trial design of roflumilast phase III trials," 2011, Athens Jun. 7-10, 2011, Poster, 1 page.
FDA PADAC Roflumilast, Questions and Answers presented UCM20871207, Apr. 2010, 27 pages.
Fialkov, *Chemical Abstracts*, 1983, 98(23):603.
Fox,"Efficacy of the PDE4 inhibitor, BAY 19/8004, in tobacco smoke models of COPD in the guinea pig," *Am J Resp Crit Care Med*, 2003, 167:A91.
German, "Reliability of drop size from multi-dose eye drop bottles: is it cause for concern?," *Pub Med Resul*, 1999, 13:93-100.
Glenn, "Taste masking in oral pharmaceuticals," *Pharm Tech Europe*, 1994, pp. 24-35.
"Glossary," *Ph Eur Monograph*, 2005, 1502:1-2.
Griswold, "SB 207499 (Ariflo), a second generation phosphodiesterase 4 inhibitor, reduces tumor necrosis factor alpha and interleukin-4 production in vivo," *J. Pharm. and Exper. Therap.*, 1998, 287(2):705-711.
Grootendorst, "Reduction in sputum neurtrophil and eosinophil numbers by the PDE4 inhibitor roflumilast in patients with COPD," *Thorax*, 2007, 62:1081-87.
Grootendorst et al., "Does a single dose of the phosphodiesterase 4 inhibitor, cilomilast (15 mg), induce bronchodilation in patients with chronic obstructive pulmonary disease?," *Pulmonary_Pharmacology_and_Therapeutics*, 2003, 16:115-120.
"Guidance for Industry, Chronic Obstructive Pulmonary Disease: Developing Drugs for Treatment," 2007, 17 pages.
Hafner et al., "Additive Effects of Phosphodiesterase-4 Inhibition on Effects of rSP-C Surfactant," *AmJ Respir Crit Care Med*, 2000, 161:1495-1500.
Hahn, *Chemical Abstracts*, 1963, 58(9):8943-8944.
Hanifin, "Type 4 Phosphodiesterase inhibitors have clinical and in vitro anti-inflammatory effects in atopic dermatitis," *J Journal of Investigative Dermatology*, 1996, 107:51-56.
Hatzelmann et al., "Anti-Inflammatory and Immunomodulatory Potential of the Novel PDE4 Inhibitor Roflumilast in Vitro," *The Journal of Pharmacology and Experimental Therapeutics*, 2001, 297(1):267-279, The American Society for Pharmacology and Experimental Therapeutics.
Hauns et al., "Four-week treatment with the new PDE4 inhibitor roflumilast in patients with exercise-induced asthma: safety, efficacy and inhibition of TNF-a ex vivo," *Eur Respir J*, 2000, 16:Suppl. 31, A3805, Abstract.
Hauns et al., "Safety-related performance is not impaired by the new PDE-4 inhibitor Roflumilast," *Eur Respir J*, 2000, 16:Suppl. 31, 277S, Abstract.
Herberg et al., "Treatment with the New PDE4 Inhibitor Roflumilast Does Not Impair Vigilance and Traffic Safety," *Eur J Clin Pharmacol*, 2000, 56(2), A29, Abstract.
Hermann, "The oral, once daily phosphodiesterase 4 inhibitor roflumilast lacks relevant pharmacokinetic interactions with inhaled budesonide," *J Clin Pharmacol*, 2007, 47:1005-1013.
Hilden, "Physics of amorphous solids," *J Pharma Sciences*, 2004, 93:3-12.
Hoymann et al., "Inhibition by Roflumilast of Airway Hyper-responsiveness to Acetylcholine 48 h after Allergen Challenge in Rats," *Am J Respir Crit Care Med*, 2001, Poster Presentation, 1 page.
Hoymann et al., "Inhibition by Roflumilast of Airway Hyper-responsiveness to Acetylcholine 48H After Allergen Challenge in Rats," *Am J Respir Crit Care Med*, 2001, 163:A431, Abstract.
Hunnemeyer et al., "Pharmacokinetics of Roflumilast and its Active Metabolite Roflumilast-N-Oxide Is Not Influenced by Smoking", *Am J Respir Crit Care Med*, 2002, Poster Presentation, 1 page.
Hunnemeyer al., "Pharmacokinetics of Roflumilast and its Active Metabolite, Roflumilast-N-Oxide, Is Not Influenced by Smoking", *Am J Respir Crit Care Med*, 2002, 165:A594, Abstract.

(56) References Cited

OTHER PUBLICATIONS

Izikki et al., "Effects of Roflumilast, a Phosphodiesterase-4 Inhibitor, on Hypoxia- and Monocrotaline- Induced Pulmonary Hypertension in Rats," *The Journal of Pharmacology and Experimental Therapeutics*, 2009, 330(1):54-62, The American Society for Pharmacology and Experimental Therapeutics.
Japanese Office Action issued in JP Application No. 2003-569234, dated Sep. 14, 2007, 17 pages.
Kast, "Chapter 1: Ointment," *Pharmaceutics*, 1998, 25 pages.
Kazumasa, "Preparation of N-pyridyl-4-(benzyloxy) benzamides as cardiotonics," *Chemical Abstracts*, 1988, 108(15):Abstract No. 131583p.
Keene et al., "Statistical analysis of COPD exacerbations," *Eur Respir J*, 2008, 32:1421-22.
Keene et al., "Statistical analysis of exacerbation rates in COPD:Tristan and Isolde revisited," *Eur Respir J*, 2008, 32:17-24.
Keipert et al., "Wechselwirkungen zwischen makromolekularen hilfsstoffen and arzneistoffen," *Pharmazie*, 1986, 41:400-404 (English abstract included—p. 1).
Kessler et al., "Patient understanding, detection and experience of COPD exacerbations: An observational, interview-based study," *Chest*, 2006, 130:133-42.
Korean Office Action issued in KR Application No. 10-2004-7012904, dated Oct. 7, 2010, 14 pages.
Kumar et al., "Inhibition of inflammation and remodeling by roflumilast and dexamethasone in murine chronic asthma," *J Pharmacol Exp Ther*, 2003, 307:349-355.
Kurashima et al., "A pilot study of surfactant inhalation for the treatment of asthmatic attack," *Jpn J Allergol*, 1991, 40:160-163.
Lahu et al., "Effect of steady-state enoxacin on single-dose pharmacokinetics of roflumilast and roflumilast," *J Clin Pharm*, 2011, 51:586-593.
Lahu et al., "Effects of steady-state enoxacin on single-dose pharmacokinetics of roflumilast and roflumilast N-oxide," ERS Sep. 2009 Poster, 2009, 1 page.
Lahu et al., "Modeling and simulation in successful drug development Programs: characterization of exacerbation reduction with roflumilast to corroborate the importance of defining patient subsets in COPD," ERS Sep. 2011 Modelling Simulation, 2011, 1 page.
Lahu et al., Effects of steady-state enoxacin on single-dose pharmacokinetics of roflumilast and roflumilast N-oxide, *J. Clin. Pharm.*, originally published online May 2010, 8 pages.
Lanes, *Am J Respir Crit Care Med*, 2008, 178:543-44.
Leichtl et al., "Efficacy of Once-Daily Roflumilast, a New, Orally Active Selective Phosphodiesterase 4 Inhibitor, in Chronic Obstructive Pulmonary Disease", *Am J Respir Crit Care Med*, May 2002, 165:A229.
Leichtl et al., "Efficacy of Once-Daily Roflumilast, a New, Orally Active, Selective Phosphodiesterase 4 Inhibitor, in Chronic Obstructive Pulmonary Disease," May 2002, poster, 1 page.
Lewis et al., "The physical and chemical stability of suspensions of sustained-release diclofenac microspheres," *Microencapsulation*, 1998, 15:5-567.
Lipworth, "Phosphodiesterase-4 inhibitors for asthma and chronic obstructive pulmonary disease," *Lancet*, 2005, 365:167-175.
Macintyre, "Chronic obstructive pulmonary disease," *Pharmacotherapy*, 2004, 24(5):33S-43S.
Mahler, "The measurement of dyspnea, contents, interobserver agreement and physiologic correlates of two new clinical indexes," *Chest*, 1984, 85:751-58.
Martin, "PDE4 inhibitors—A review of the recent patent literature," *IDrugs*, 2001, 4(3):312-338, PharmaPress Ltd.
Meyer, "Charackterisierung und Beeinflussung der Losungseigenschaften von 6-Bromcip," Dissertation 1995, 1995, pp. 154-189 (English summary included).
Müller, Pharmazeutische Technologie Moderne Arzneiformen, 1997, pp. 80-91.

Muise et al., "Comparison of inhibition of ovalbumin-induced bronchoconstriction in guinea pigs and in vitro inhibition of tumor necrosis factor-a formation with phosphodiesterase 4 (PDE4) selective inhibitors," *Biochem Pharmacol*, 2002, 63:1527-35.
Nassr et al., "Effects of CYP3A4 by Rifampicin on the Pharmacokinetics of roflumilast and roflumilast N-oxide," German pharmacology Meeting, Wurzburg, 2006, Poster, Rifampicin Roflumilast, 1 page.
Nell et al., "Acute Anti-Inflammatory Effect of the Novel Phosphodiesterase 4 Inhibitor Roflumilast on Allergen Challenge in Asthmatics After a Single Dose," *Am J Respir Crit Care Med*, 2000, 161(3):Part 2, A200, Abstract.
Norman, "PDE4 inhibitors 1999," *Expert Opinion Therapeutic Patents*, 1999, 9(8):1101-1118.
O'Donnell et al., "Canadian thoracic society recommendations for management of chronic obstructive pulmonary disease—2008 update—highlights for primary care," *Can Respir J*, 2008, 15:Suppl A P, 1A-8A.
Odian, *Principles of polymerization*, Wiley and Sons, 1991, pp. 19-23.
Philippine Office Action issued in PH Application No. 1-2004-501237, dated Jun. 16, 2009, 5 pages.
Opposition filed in the name of Hexal AG against EP1478399 of Nycomed GmbH, filed Feb. 20, 2003, granted Mar. 21, 2012, 8 pages.
Pfizer Centre Source, "Dexamethasone USP Micronized," 2010, 5 pages.
*Pharmacy*, 4th ed., pp. 114-117 Dec. 2000,The Peoples Medical Publishing House, edited by Bi Dianzhou.
Pleiss et al., "Synthesis of [18F] Labelled Roflumilast using difluoro [18F] bromomethane as alkylating agent," *Synth. Appl. Isotop. Lab. Comp.*, 2000, 7:375-376.
Poppe et al., "Effects of a Selective PDE4-Inhibitor AWD 12-281 in Comparison With SB 207499 and Roflumilast on Tracheal Phenol Red Secretion in Mice and LPS-Induced Neutrophilia in BAL in Lewis Rats and Domestic Pigs," *Am J Respir Crit Care Med*, 2001, 163(5): A, Abstract.
Pruniaux, "Efficacy of a selective phosphodiesterase 4 inhibitor, CI-1044, on cigarette smoke-induced emphysema development in mice," *Am J Resp Crit Care Med*, 2003, 167:A874.
PVP disclosure—downloaded from the internet, Jan. 21, 2008, 2 pages.
Quanjer et al., "Lung volumes and forced ventilatory flows," *Eur Respir J*, 1993, 6(suppl): 5-40.
Rabe, "Global strategy for the diagnosis, management and prevention of chronic obstructive pulmonary disease," *J Respir Crit Care Med*, 2007, 176:532-55.
Rabe et al., "Theophylline and selective PDE inhibitors as bronchodilators and smooth muscle relaxants," *Eur Respir J*, 1995, 8:637-42.
Rabe, "Roflumilast for the treatment of chronic obstructive pulmonary disease," *Expert Reviews Resp Med*, 2010, 4:543-555.
Rabe et al., "Roflumilast—an orla anti-inflammatory treatment for chronic obstructive pulmonary disease: a randomized controlled trial," *Lancet*, 2005, 366:563-71.
Rabe, "Correspondence," *Lancet*, 2005, 366:1846-1847.
Rabin, "EQ-SD: a measure of health status from the EuroQol Group," *Ann Med*, 2001, 33:337-43.
Reid, "Roflumilast," *Current Opinion in Investigational Drugs*, 2002, 3(8):1165-1170.
Reid, "Cytokines in the pathogenesis of chronic obstructive pulmonary disease," *Current Pharmaceutical Design*, 2003, 9:25-38.
*Remington: The Science and Practice of Pharmacy*, vol. II, Mack Publishing Company, Easton, Pennsylvania, 1995, pp. vii-viii and 1618-1629.
Rennard, "Reduction of exacerbations by the PDE4 inhibitor roflumilast—the importance of defining different subsets of patients with COPD," *Respiratory Research*, 2011, 18:12.
Response to EPO Communication Pursuant to Article 94-3 in EP Application No. 03704652.1, 2009, 27 pages.
Roflumilast—Daliresp Full Prescribing Information, FDA, 2011, 14 pages.

(56) References Cited

OTHER PUBLICATIONS

Roflumilast—European Approval Documents Daxas, "Summary of Product Characteristics," Annex 1, 2010, 11 pages.
Roflumilast—European Approval Documents Daxas, Package Leaflet, "Information for the User-Daxas 500 Micrograms Film-coated Tablets," 2010, 7 pages.
Rolando, "The ocular surface and tear film and their dysfunction in dry eye disease," *Survey of Ophthalmology*, 2001, 45:S203-S210.
Safety data sheet CRODESTA F10-HB03671 Sucrose Distearate Croda Europe Ltd, 2005, 1 page.
Safety data sheet CRODESTA F110 HB03722Sucrose Stearate and Sucrose Stearate Croda Europe Ltd, 2005, 1 page.
Safety data sheet CRODESTA F160 HB03750 Sucrose Stearate Croda Europe Ltd, 2005, 1 page.
Safety data sheet CRODESTA F20 HB03668 Sucrose Distearate Croda Europe Ltd, 2005, 1 page.
Safety data sheet CRODESTA F50 HB03669 Sucrose Distearate Croda Europe Ltd, 2005, 1 page.
Safety data sheet CRODESTA SL40 HB03791 Aqua and Sucrose Cocoate and Alcohol Croda Europe Ltd, 2005, 1 page.
Schmidt., "The phosphodiesterase 4 inhibitor roflumilast is effective in the treatment of allergic rhinitis," *J Allergy Clin Immunol*, 2001, 108(4):30-536, Mosby, Inc.
Sin et al., "Skeletal muscle weakness, reduced exercise tolerance, and COPD: Is systemic inflammation the missing link?", *Thorax*, 2006, 61:1-3.
Sin and Man, "Systematic inflammation and mortality in chronic obstructive pulmonary disease," *Can J Phsiol Pharmacol* ,2007, 85:141-47.
Singh et al., "Long-term use of inhaled-corticosteroids and the risk of pneumonia in chronic obstructive pulmonary disease," *Arch Intern Med*, 2009, 169: 219-229.
Snoeck-Stroband et al, "Chronic bronchitis sub-phenotype within COPD: inflammation in sputum and biopsies," *Eur Respir J*, 2008, 31:70-77.
Soler-Cataluna, "Severe acute exacerbations and mortality in patients with chronic obstructive pulmonary disease," *Thorax*, 2005, 60:925-31.
Solutol HS 15 Technical Information, BASF, Jul. 2003, 8 pages.
Sorbera., "Roflumilast: Antiallergy/Antiasthmatic Treatment of COPD Phosphodiesterase 4 Inhibitor", *Drugs of the Future*, 2000, 25(12):1261-1264.
Spencer et al., "Health status deterioration in patients with chronic obstructive pulmonary disease," *Am J Respir Crit Care Med*, 2001, 163:122-128.
Spina, "PDE4 inhibitors: current status," *J Pharmacol*, 2008, 155:308-15.
Stebbins et al., "Aerosol activity of phosphodiesterase type IV inhibitors in a murine model of cigarette smoke induced pulmonary inflammation," *Am J Resp Crit Care Med*, 2003, 167:A486.
Stockley, "Addition of salmeterol to existing treatment in patients with COPD: a 12 month study," *Thorax*, 2006, 61:122-28.
Strickley, "Solubilizing excipients in oral and injectable formulations," *Pharmaceutical Research*, 2004, 212:201-230.
Sucker et al., Pharmazeutische Technologie: Beschrelbung der Arznelformen Spezielle Entwicklung der Dermatika, 1978, pp. 629-636 and pp. 650-665.
Suissa et al., "Passive smoking and asthma death," *Eur Respir J*, 2008, 32:1117-18.
Szafranski et al., "Efficacy and safety of budesonide/formoterol in the management of chronic obstructive pulmonary disease," *Eur Respir J*, 2003, 21:74-81.
Tashkin et al., "A 4-year trial of tiotropium in chronic obstructive pulmonary disease," *N Engl J Med*, 2008, 359:1543-54
Tenor et al, "Pharmacology, Clinical Efficacy, and Tolerability of Phosphodiesterase-4 Inhibitors: Impact of Human Pharmacokinetics", *Handbook of Experimental Pharmacology*, 2011, pp. 85-119.
Thurlbeck, "Measurement of pulmonary emphysema," *American Review Respiratory Disease*, 1967, 95(5):752-764.

Timmer et al, "Safety and Efficacy of the New PDE4 Inhibitor Roflumilast Administered to Patients with Exercise-Induced Asthma Over 4 Weeks," *Am J Respir Crit Care Med*, 2000, 161(3):Part 2, A505, Abstract.
Timmer et al., "The Clinical Efficacy of the New PDE4 Inhibitor Roflumilast in Exercise-Induced Asthma is Accompanied by Suppression of LPS-Stimulated TNF-a Levels," *Europ J Clin Pharm*, 2000, 56(2):A29, Abstract.
Timmer et al., "Treatment with Therapeutic Doses of the New PDE4 Inhibitor Roflumilast Does Not Influence Cardiovascular Function", *Europ J Clin Pharm*, 2000, 56(2):A29, Abstract.
Toshiro et al., *Yakuzai-gaku* (*Pharmaceutics*) issued by Konando, 1997, 5th edition, pp. 112 to 114 (with English translation).
Tros de Ilarduya et al., "Solubilization and Interaction of Sulindac with Polyvinylpyrrolidone K30 in the Solid State and in Aqueous Solution," *Drug Development and Industrial Pharmacy*, 1998, 24(3):295-300.
Von Richter, "Effect of fluvoxamine on the pharmacokinetics of roflumilast and roflumilast N-Oxide," *Clin Pharmacoklnet*, 2007, 46:613-622.
Washington, "Ocular drug delivery," *Ocular drug delivery particulates*, 2000, p. 265, 16 total pages.
Wedzicha et al., "The prevention of chronic obstructive pulmonary disease exacerbations by salmeterol/fluticasone propionate or tiotropium bromide," *Am J Respir Crit Care Med*, 2008, 177: 19-26.
Weimar et al., "No Interaction of Roflumilast, a New, Orally Active, Selective PDE4 Inhibitor, with Inhaled Salbutamol," *Eur Respir J*, 2001, Poster Presentation, 1 page.
Weimar et al., "No interaction of roflumilast, a new, orally active, selective PDE4 inhibitor, with inhaled salbutamol", *Eur Respir J*, 2001, vol. 18, Suppl. 33, 156s, Abstract.
Wollin et al., "Inhibition by Roflumilast of Airway Hyper-responsiveness to Adenosine and Pulmonary Inflammation in Allergen-challenged Brown Norway Rats," *Eur Respir J*, 2001, Poster Presentation, 1 page.
Wollin et al., "Inhibition by Roflumilast of Airway Hyper-responsiveness to Adenosine and Pulmonary Neutrophil Accumulation 3H After Allergen Challenge in Rats," *Am J Respir Crit Care Med*, 2001, 63:A432, Abstract.
Wollin et al., "Inhibition by roflumilast of airway hyperresponsiveness to adenosine and pulmonary inflammation in allergen challenged Brown-Norway rats", *Eur Respir J*, 2001,18:Suppl. 33, 35s, Abstract.
Yagupolskii, *Chemical Abstracts*, 1961, 55:18.
Yliruusi et al., "A new Method to evaluate the elastic behavior of tablets during compression," *Drug: Dev. Ind. Pharm.*, 1997, 23(1):63-68.
Zech et al., "High oral bioavailabiity of roflumilast, a new, orally active once daily PDE4 inhibitor," *Eur Respir J*, 2001, 11 pages.
Zech et al., "High oral absolute bioavailability of roflumilast, a new, orally active, once daily PDE4 inhibitor", , *Eur Respir J*, 2001, 18:Suppl. 33, 20s, Abstract.
Zelko et al., "Effects of storage conditions on the free volume of polyvinylpyrrolidone: comparison of positron lifetime data with tensile strength of tablet," *Pharm. Res.*, 2000, 17(8):1030-1032.
ZuWallack et al., "Salmeterol plus theophylline combination therapy in the treatment of COPD," *Chest*, 2001, 119:1661-70.
Applicant Appeal Brief filed in U.S. Appl. No. 12/149,250, filed Mar. 21, 2011, 20 pages.
Applicant Appeal Brief filed in U.S. Appl. No. 10/515,896, filed Jan. 26, 2011, 37 pages.
Applicant Appeal Brief filed in U.S. Appl. No. 11/662,887, filed Feb. 2, 2012, 33 pages.
Applicant Appeal Brief filed in U.S. Appl. No. 10/505,138, filed Mar. 30, 2009, 40 pages.
Applicant Appeal Briefs filed in U.S. Appl. No. 10/515,698, filed Aug. 26, 2009 and Oct. 26, 2009, 34 pages.
Applicant Reply Brief filed in U.S. Appl. No. 10/515,896, dated Jun. 13, 2011, 26 pages.
Applicant Reply Brief filed in U.S. Appl. No. 11/662,887, filed May 30, 2012, 13 pages.
Applicant Reply Brief filed in U.S. Appl. No. 10/515,698, filed Mar. 29, 2010, 11 pages.

(56) References Cited

OTHER PUBLICATIONS

Applicant Reply Brief filed in U.S. Appl. No. 10/505,138, filed Aug. 3, 2009, 37 pages.
USPTO Final Office Action issued in U.S. Appl. No. 11/501,836, dated May 7, 2010, 13 pages.
USPTO Non-Final Office Action issued in U.S. Appl. No. 11/501,836, dated Aug. 7, 2009, 12 pages.
USPTO Non-Final Office Action issued in U.S. Appl. No. 11/501,836, dated Feb. 29, 2012, 9 pages.
USPTO Non-Final Office Action issued in U.S. Appl. No. 12/876,996, dated Feb. 29, 2012, 15 pages.
USPTO Non-Final Office Action issued in U.S. Appl. No. 13/008,842, dated Jan. 4, 2012, 12 pages.
USPTO Non-Final Office Action issued in U.S. Appl. No. 11/501,836, dated Mar. 20, 2009, 7 pages.
USPTO Non-final Office Action issued in U.S. Appl. No. 12/149,250, dated Apr. 20, 2010, 13 pages.
USPTO Non-final Office Action issued in U.S. Appl. No. 10/433,398, dated Jan. 11, 2006, 14 pages.
USPTO Non-final Office Action issued in U.S. Appl. No. 10/515,698, dated Jan. 23, 2008, 14 pages.
USPTO Final Office Action issued in U.S. Appl. No. 10/515,698, dated Aug. 19, 2008, 9 pages.
USPTO Restriction Requirement issued in U.S. Appl. No. 10/515,896, dated Mar. 13, 2009, 6 pages.
USPTO Final Office Action issued in U.S. Appl. No. 10/515,896, dated Mar. 26, 2010, 20 pages.
USPTO Non-final Office Action issued in U.S. Appl. No. 11/642,621, dated May 19, 2010, 14 pages.
USPTO Non-final Office Action issued in U.S. Appl. No. 11/885,837, dated Sep. 14, 2010, 13 pages.
USPTO Final Office Action issued in U.S. Appl. No. 12/149,250, dated Oct. 27, 2010, 8 pages.
USPTO Restriction Requirement issued in U.S. Appl. No. 10/515,698, dated Oct. 9, 2007, 9 pages.
USPTO Final Office Action issued in U.S. Appl. No. 10/505,138, dated Feb. 2, 2006, 10 pages.
USPTO Final Office Action issued in U.S. Appl. No. 10/505,138, dated May 30, 2007, 7 pages.
USPTO Final Office Action issued in U.S. Appl. No. 10/505,138, dated Oct. 16, 2008, 8 pages.
USPTO Final Office Action issued in U.S. Appl. No. 10/505,138, dated Nov. 12, 2008, 8 pages.
USPTO Patent Board Decision issued in U.S. Appl. No. 10/505,138, dated Oct. 20, 2010, 19 pages.
USPTO Examiner's Answer to Appeal Brief issued in U.S. Appl. No. 10/505,138, dated Jun. 2, 2009, 19 pages.
USPTO Final Office Action issued in U.S. Appl. No. 11/501,836, dated Oct. 11, 2012, 73 pages.
USPTO Final Office Action issued in U.S. Appl. No. 12/876,996, dated Oct. 11, 2012, 58 pages.
USPTO Non-final Office Action issued in U.S. Appl. No. 10/505,138, dated Sep. 1, 2005, 9 pages.
USPTO Non-final Office Action issued in U.S. Appl. No. 10/505,138, dated Nov. 3, 2006, 16 pages.
USPTO Non-final Office Action issued in U.S. Appl. No. 10/505,138, dated Feb. 27, 2008, 15 pages.
USPTO Non-final Office Action issued in U.S. Appl. No. 10/531,720, dated Jan. 18, 2008, 7 pages.
USPTO Non-final Office Action issued in U.S. Appl. No. 12/292,795, dated Aug. 11, 2011, 10 pages.
USPTO Notice of Allowance issued in U.S. Appl. No. 10/505,138, dated Mar. 18, 2011, 55 pages.
USPTO Notice of Allowance issued in U.S. Appl. No. 13/008,842, dated Oct. 15, 2012, 44 pages.
USPTO Notice of Allowance issued in U.S. Appl. No. 13/008,842, dated Dec. 18, 2012, 4 pages.
USPTO Notice of Allowance issued in U.S. Appl. No. 13/008,842, dated Feb. 27, 2013, 12 pages.
USPTO Notice of Allowance issued in U.S. Appl. No. 10/531,720, dated Aug. 28, 2008, 6 pages.
USPTO Notice of Allowance issued in U.S. Appl. No. 12/292,795, dated Apr. 24, 2012, 7 pages.
USPTO Suppl Notice of Allowability issued in U.S. Appl. No. 10/531,720, dated Nov. 7, 2008, 4 pages.
USPTO Final Office Action issued in U.S. Appl. No. 11/642,621, dated Nov. 1, 2010, 8 pages.
USPTO Notice of Allowance issued in U.S. Appl. No. 11/642,621, dated Jan. 24, 2011, 6 pages.
USPTO Restriction Requirement in U.S. Appl. No. 11/642,621, dated May 15, 2009, 9 pages.
USPTO Final Office Action issued in U.S. Appl. No. 10/433,398, dated Jul. 3, 2006, 9 pages.
USPTO Notice of Allowance issued in U.S. Appl. No. 10/433,398, dated Sep. 21, 2006, 5 pages.
USPTO Final Office Action issued in U.S. Appl. No. 10/515,698, dated Jan. 16, 2009, 7 pages.
USPTO Examiner's Answer to Appeal Brief issued in U.S. Appl. No. 10/515,698, dated Feb. 2, 2010, 11 pages.
USPTO Patent Board Decision issued in U.S. Appl. No. 10/515,698, dated Jun. 27, 2011, 8 pages.
USPTO Non-final Office Action issued in U.S. Appl. No. 13/219,056, dated Oct. 19, 2011, 18 pages.
USPTO Final Office Action issued in U.S. Appl. No. 13/219,056, dated Apr. 25, 2012, 10 pages.
USPTO Examiner's Answer to Appeal Brief issued in U.S. Appl. No. 12/149,250, dated Jun. 8, 2011, 10 pages.
USPTO Non-final Office Action issued in U.S. Appl. No. 10/515,896, dated Jun. 23, 2009, 17 pages.
USPTO Non-final Office Action issued in U.S. Appl. No. 10/515,896, dated Sep. 14, 2010, 26 pages.
USPTO Examiner's Answer to Appeal Brief issued in U.S. Appl. No. 10/515,896, dated Apr. 14, 2011, 31 pages.
USPTO Patent Board Decision issued in U.S. Appl. No. 10/515,896, dated Jun. 13, 2013, 18 pages.
USPTO Non-final Office Action issued in U.S. Appl. No. 11/662,887, dated Jun. 28, 2010, 18 pages.
USPTO Non-final Office Action issued in U.S. Appl. No. 11/662,887, dated Dec. 16, 2010, 16 pages.
USPTO Final Office Action issued in U.S. Appl. No. 11/662,887, dated Jun. 8, 2011, 12 pages.
USPTO Examiner's Answer to Appeal Brief issued in U.S. Appl. No. 11/662,887, dated Mar. 30, 2012, 19 pages.
USPTO Restriction Requirement issued in U.S. Appl. No. 11/662,888, dated Sep. 15, 2008, 8 pages.
USPTO Restriction Requirement issued in U.S. Appl. No. 11/885,837, dated Jun. 8, 2010, 9 pages.
USPTO Final Office Action issued in U.S. Appl. No. 11/885,837, dated Mar. 21, 2011, 11 pages.
USPTO Non-final Office Action issued in U.S. Appl. No. 11/885,837, dated May 23, 2013, 9 pages.
USPTO Notice of Allowance issued in U.S. Appl. No. 13/547,945, dated May 2, 2013, 40 pages.
USPTO Notice of Allowance issued in U.S. Appl. No. 13/547,945, dated Jul. 22, 2013, 13 pages.
USPTO Non-Final Office Action issued in U.S. Appl. No. 13/860,264, dated Jun. 12, 2013, 31 pages.
USPTO Non-Final Office Action issued in U.S. Appl. No. 13/860,248, dated Jun. 12, 2013, 29 pages.
USPTO Notice of Allowance issued in U.S. Appl. No. 13/008,842, dated Jan. 28, 2013, 5 pages.
Borst et al., "New and extended applications for USP drug release apparatus 3," Dissolution Technologies, Feb. 1997, 6 pages.
Bühler, *Kollidon: Polyvinylpyrrolidone for the pharmaceutical industry*, BASF, 4th edition, Mar. 1998, 24 pages (insert).
Bühler, *Kollidon: Polyvinylpyrrolidone for the pharmaceutical industry*, BASF, 4th edition, Mar. 1998, 288 pages (complete book).
"Dissolution," USP 36—Physical Tests / (711) Dissolution 1, Nov. 2012, 7 pages.

(56) References Cited

OTHER PUBLICATIONS

"Dissolution Methods—List of all Drugs in the Database," Retrieved via Internet Archive WayBackMachine on Feb. 13, 2014, Accessible at URL<http://www.accessdata.fda.gov/scripts/cder/dissolution/dsp_SearchResults_Dissolutions.cfm>. 30 pages.
"Dissolution Methods—Search results for 'roflumilast,'" Retrieved from the Internet on Feb. 17, 2014. Accessible at URL< http://www.accessdata.fda.gov/scripts/CDER/dissolution/dsp_SearchResults_Dissolutions.cfm>. 1 page.
Dyas and Shah, "Dissolution and dissolution testing," *Encyclopedia of Pharmaceutical Technology*, 2007, 21 pages.
Glossary Terms, Definition of Immediate Release, Oct. 26, 2009, 2 pages.
*Handbook of Pharmaceutical Excipients*, Ed. Rowe et al., 4th edition, Pharmaceutical Press, 2003, 11 pages.
*Handbook of Pharmaceutical Excipients*, Sodium Starch Glycolate, Ed. Wade and Weller, Pharmaceutical Press, 1994, 7 pages.
Kukura et al., "Shear distribution and variability in the USP apparatus 2 under turbulent conditions," *Int. J Pharm*, 2004, 279:9-17.
Opposition filed in the name of Hexal AG against EP2258394B1 of Takeda GmbH (including Annex VI), filed Feb. 17, 2014, patent granted May 15, 2013, 29 pages.
Opposition filed in the name of Mylan against EP2258394B1 of Takeda GmbH, patent granted May 15, 2013, filed Feb. 17, 2014, 20 pages.
*Pharmaceutics: The Science of Dosage Form Design*, Ed. Aulton, 1st edition, Churchill Livingstone, 1988, 33 pages.
*Pharmaceutics: The Science of Dosage Form Design*, Ed. Aulton, 2nd edition, Churchill Livingstone, 2002, 4 pages.
Wikipedia [online]. "Dissolution testing," Oct. 2013 [retrieved on Dec. 18, 2013]. Retrieved from the Internet: URL<http//en.wikipedia.org/wiki/Dissolution_testing>. 3 pages.
Wikipedia [online]. "Polyvinylpyrrolidon," Dec. 2013 [retrieved on Feb. 12, 2014]. Retrieved from the Internet: URL<http://de.wikipedia.org/wiki/Polyvinylpyrrolidon>. 9 pages (with English translation).
USPTO Non-final Office Action issued in U.S. Appl. No. 13/216,936, dated Feb. 26, 2014, 39 pages.
USPTO Non-final Office Action issued in U.S. Appl. No. 14/038,666, dated Dec. 19, 2013, 36 pages.
USPTO Non-final Office Action issued in U.S. Appl. No. 14/038,678, dated Dec. 17, 2013, 41 pages.
USPTO Notice of Allowance issued in U.S. Appl. No. 13/860,264, dated Sep. 3, 2013, 9 pages.
USPTO Notice of Allowance issued in U.S. Appl. No. 13/860,248, dated Sep. 6, 2013, 38 pages.
USPTO Patent Board Decision issued in U.S. Appl. No. 12/149,250, dated Sep. 11, 2013, 11 pages.
USPTO Notice of Allowance issued in U.S. Appl. No. 11/885,837, dated Nov. 6, 2013, 9 pages.
Written Submission Further to Proprietor's Submissions of Jul. 31, 2103 and Summons to Attend Oral Proceedings of Jan. 3, 2014, communication submitted by Hexal AG in EP Application No. EP1478399 on Mar. 13, 2014, 22 pages.
EPO Opposition against EP1478399, Opponent Hexal AG, Additional responses filed prior to Oral Proceedings, dated May 7, 2014 (33 pages).
EPO Annexes to Minutes Oral Proceedings Opposition received at EPO Apr. 25, 2014, including claims, main request and auxiliary requests (18 pages).
EPO Meeting Minutes Oral Proceedings Opposition before EPO, Application No. 03704652.1, dated Jul. 16, 2014 (4 pages).
EPO Minutes of the oral proceedings before the Opposition Division, Application No. 03704652.1, dated May 13, 2014 (2 pages).
EPO Revocation Decision re Oral Proceedings dated Jul. 16, 2014 (2 pages).
EPO Summary of Facts and Submissions Grounds for Decision, Application No. 03704652.1, dated Jul. 16, 2014 (19 pages).
EPO Information Announcement regarding outcome of oral proceedings of May 13, 2014, Application No. 03704652.1 (1 page).
Krowczynski, "An outline of the drug form technology", Manual for students of pharmacy, Edition 1, pp. 408-409 (1974) (original and English translation attached).
Nakayama et al., "Saikinno-hifugaiyozai (Latest External Dermatologic Agents)", pp. 152-153, 171, 187 (1991) (original and English translation attached).
Parikh, Handbook of Pharmaceutical Granulation Technology, pp. 63-64 (1997).
Rybacki et al., Excipient in Drug Form Technology, Pharmacist's Library, vol. 7, pp. 36-39 (Warsaw 1980) (original and English translation attached).
Tousey, "The Granulation Process 101 Basic Technologies for Tablet Making", Pharmaceutical Technology Tableting & Granulation, pp. 8-13 (2002).
USPTO Non-Final Office Action dated Feb. 26, 2014 in U.S. Appl. No. 13/216,936 (39 pages).
USPTO Final Office Action dated Aug. 26, 2014 in U.S. Appl. No. 13/216,936 (12 pages).
USPTO Final Office Action dated Jun. 18, 2014 in U.S. Appl. No. 14/038,666 (13 pages).
USPTO Advisory Action dated Sep. 10, 2014 in U.S. Appl. No. 14/038,666 (3 pages).
USPTO Non-Final Office Action dated Jun. 27, 2014 in U.S. Appl. No. 14/038,678 (8 pages).
USPTO Non-Final Office Action dated Sep. 16, 2014 in U.S. Appl. No. 14/075,035 (7 pages).
USPTO Non-final Office Action dated Nov. 14, 2013, issued in U.S. Appl. No. 13/739,457, filed Jan. 11, 2013, 49 pages.
EPO Summons to attend oral proceedings in EP Application No. 03704652.1-1464/1478399, dated Jan. 3, 2014 (9 pages).
EPO Summary of Facts and Submissions in EP Application No. 10 173 234.5, dated Feb. 17, 2015 (18 pages).
Foye's Principles of Medicinal Chemistry, $5^{th}$ ed., Williams and Lemke (eds)., 2002, p. 157.
Handbook of Pharmaceutical Excipients, Washington, D.C., American Pharmaceutical Association, 2000, pp. 305-308.
Handbook of Pharmaceutical Excipients, Washington, D.C., American Pharmaceutical Association, 2000, pp. 433-439.
Lee and Han, Principles and Technologies of the Preparation of Dosage Forms, 2002, pp. 150-151 (with English translation).
Pharmaceutical Dosage Forms, $2^{nd}$ ed., Lieberman, Lachman and Schwartz (eds)., 1990, pp. 135, 174-175 and 268.
Remington's Pharmaceutical Science, $20^{th}$ ed., Gennaro (ed)., 2000, p. 851 (with English translation).
Voigt and Terborg, "Granulometric determination of the effect of polyvinylpyrrolidone on the solubility of difficultly soluble drugs," Pharmazie, 1980, 35:311-312 (with English translation).
"Impurity Guidance Federal Register," FDA, 2000, 65(140):45085-45090.
"Roflumilast—phase change II—Drug News Report," ProQuest Dialog, 2000, 2 pages.
"Guideline for Submitting Supporting Documentation in Drug Applications for the Manufacture of Drug Substances," CDER FDA, 1987, 48 pages.
Ashton et al., "Selective Type IV Phosphodiesterase Inhibitors as Antiasthmatic Agents. The Syntheses and Biological Activities of 3-(Cyclopentyloxy)-4-methoxybenzamides and Analogues," J Med Chem., 1994, 37(11):1696-1703.
Baxter et al., "Mechanistic Aspects of Carbon Monoxide Formation form Volatile Anesthetics," Anesthesiol., 1998, 89:929-941.
CHMP assessment report for Roflumilast, procedure number EMEA/H/C/00179, European Medicines Agency, Apr. 22, 2010, 46 pages.
Committee for Proprietary Medicinal Products, "Note for Guidance on the Investigation of Bioavailability and Bioequivalence," The European Agency for the Evaluation of Medicinal Products, Jul. 26, 2001, 19 pages.
Committee for Proprietary Medicinal Products, "Note for Guidance on Quality of Modified Release Products," The European Agency for the Evaluation of Medicinal Products, Jul. 29, 1999, 16 pages.

(56) References Cited

OTHER PUBLICATIONS

European Exhibit D35, Pharmaceutical Excipients p. VI, Peter C. Schmidt, in European Patent No. 2258394, dated Sep. 16, 2015, 5 pages (with English translation).
European Exhibit D43, Expert Opinion on the Study of Professor Dr. Stefan Hockertz Eurotox reg. Toxicologist, in European Patent No. 2258394, dated May 2, 2014, 12 pages (with English translation).
European Exhibit D44, Roflumilast Direct Compression, in European Patent No. 2258394, dated Sep. 16, 2015, 9 pages.
European Exhibit D45, Hexal AG Pharmaceutical Development, Roflumilast test report, in European Patent No. 2258394, dated Sep. 9, 2015, 4 pages (in English and German).
European Letter In Preparation of Oral Proceedings to be Held on Nov. 16 and 17, 2015 in Opposition Proceedings in European Patent No. 2258394, dated Sep. 16, 2015, 20 pages.
European Reply to Summons to the Oral Proceedings of Feb. 17, 2015 in European Patent No. 2258394, dated Sep. 16, 2015, 37 pages.
Expert Opinion of Prof. Dr. Wolfgang Frieβ with Short Curriculum Vitae in European Patent No. 2258394, dated Sep. 15, 2015, 10 pages.
Giembycz, "Development status of second generation PDE4 inhibitors for asthma and COPD: the story so far," Monaldl Arch Chest Dis., 2002, 57(1):48-64.
Guidance for Industry, Dissolution Testing of Immediate Release Solid Oral Dosage Forms, U.S. Department of Health and Human Services, Aug. 1997, 17 pages.
Karlsson, et al., "Chpt 18:Anti-inflammatory Effects of Novel Selective Cyclic Nucleotide Phosphodiesterase Inhibitors," T-Lymphocyte and Inflammatory Cell Research in Asthma, 1993, pp. 323-351.
Korean Text Book Pharmaceutical Dosage Form 1996—original Pharmaceutical Dosage Forms•—Author(s): Special Interest Group on Pharmaceutics, Korean Association of Colleges of Pharmacy; Publication Date: Mar. 2, 1996, 4 pages (original and English translation attached).
Kwong et al., "Formulation assessment of MK-886, a poorly water-soluble drug, in the beagle dog," Int J Pharma., 1994, 103:259-265.
Reeves et al., "The identification of a new cyclic nucleotide phosphodiesterase activity in human and guinea-pig cardiac ventricle," Biochem J., 1987, 241:535-541.
Souness et al., "Pig aortic endothelial-cell cyclic nucleotide phosphodiesterases: Use of phosphodiesterase inhibitors to evaluate their roles in regulating cyclic nucleotide levels in intact cells," Biochem J., 1990, 266:127-132.
Stawiski et al., "Ro 20-1724: An Agent that Significantly Improves Psoriatic Lesions in Double-Blind Clinical Trials," J Investig Dermatol., 1979, 73(4):261-263.
EPO Summons to attend oral proceedings in EP Application No. 10173234.5, dated Feb. 17, 2015, 18 pages.
Reply by HEXAL to Grounds of Appeal by TAKEDA—EP1478399, dated Jun. 12, 2015, 34 pages.
Response to Official Action and data filed Nov. 9. 2009 in corresponding European Patent Application No. 03704652.1-2123, 27 pages.
USPTO Final Office Action issued in U.S. Appl. No. 13/216,936, dated Jul. 28, 2015, 10 pages.
USPTO Final Office Action issued in U.S. Appl. No. 14/038,678, dated Dec. 5, 2014, 8 pages.
USPTO Non-final Office Action issued in U.S. Appl. No. 14/038,666, dated Jul. 2, 2015, 7 pages.
USPTO Non-final Office Action issued in U.S. Appl. No. 14/735,004 dated Jul. 30, 2015, 9 pages.
USPTO Non-final Office Action issued in U.S. Appl. No. 14/735,015 dated Jul. 31, 2015, 11 pages.
sepia.unil.ch' [online]. "Pharmakokinetics," last updated Jul. 2009. Retrieved from the Internet: URL <http://sepia.unil.ch/pharmacology/index.php?id=100&L=0>. 4 pages.

Altana International Analysts & Press Conference, Bad Homburg, Aug. 22, 2001, 46 pages.
Decision by Opposition division Revoking EP 2258394, dated Dec. 12, 2015, 2 pages.
Drug Effects—Textbook of Pharmaclogy and Toxicology, 7th Edition, Mutschler (ed)., 1997, p. 37 (with English translation).
European Exhibit D48, Avicel for solid dose forms, in European Patent No. 2258394, dated Feb. 10, 2015, 2 pages.
European Exhibit D49, Official Journal of the European Union, in European Patent No. 2258394, dated Feb. 20, 2004, 16 pages.
European Exhibit D50, ICH Harmonised Tripartite Guideline, in European Patent No. 2258394, dated Oct. 27, 1994, 4 pages.
European Exhibit D55, Cross-Discipline Team Leader Review, in European Patent No. 2258394, dated Apr. 28, 2010, 35 pages.
European Letter In Preparation of Oral Proceedings and in Reply to the Submission of Opponent O2 of Sep. 16, 2015, in Opposition Proceedings in European Patent No. 2258394, dated Oct. 16, 2015, 59 pages.
Herlich et al., "The Non-GLP Toleration/Dose Range Finding Study: Design and Methodology Used in an Early Toxicology Screening Program," Proc. West. Pharmacol. Soc., 2009, 94-98.
Meeting Minutes Oral Proceedings Opposition Proceedings in European Patent No. 2258394, dated Dec. 14, 2015, 5 pages.
Note for Guidance on Safety Pharmacology Studies for Human Pharmaceuticals, European Medicines Agency, Jun. 2001, 10 pages.
Reasoning for the Rejection Decision by Opposition Division in European Patent No. 2258394, dated Dec. 14, 2015, 20 pages.
Spindler and Seiler, "Quality management of pharmacology and safety pharmacology studies," Fundamental & Clinical Pharmacology, 2002, 16:83-90.
Submission by Hexal AG against EP2258394B1, dated Nov. 3, 2015, 10 pages.
Declaration of Joseph M. Fortunak under Rule 1.132 dated Dec. 29, 2015 in U.S. Appl. No. 14/038,666, filed Sep. 26, 2013, 10 pages.
USPTO Final Office Action issued in U.S. Appl. No. 14/038,666, dated Jan. 22, 2016, 16 pages.
USPTO Final Office Action issued in U.S. App. No. 14/735,004, dated Feb. 9, 2016, 9 pages.
USPTO Final Office Action issued in U.S. Appl. No. 14/735,015, dated Feb. 10, 2016, 12 pages.
USPTO Non-final Office Action issued in U.S. Appl. No. 13/216,936, dated Dec. 29, 2014, 16 pages.
USPTO Non-final Office Action issued in U.S. Appl. No. 14/731,964 dated Oct. 8, 2015, 8 pages.
European Document, "Grounds for Appeal," in European Patent No. 2258394, dated Apr. 22, 2016, 35 pages.
European Exhibit D56, "Roflumilast Direct Compression," in European Patent No. 2258394, dated Apr. 22, 2016, 7 pages.
European Exhibit D57, "Expert Statement," in European Patent No. 2258394, dated Apr. 22, 2016, 4 pages.
European Exhibit D58, "Die Tablette," in European Patent No. 2258394, dated Apr. 22, 2016, 3 pages.
European Exhibit D59, "Pharmazeutische Technologie," in European Patent No. 2258394, dated Apr. 22, 2016, 5 pages.
Handbook of Pharmaceutical Excipients, Second Edition, 1994, pp. 392-399.
USPTO Final Office Action issued in U.S. Appl. No. 14/731,964, dated Apr. 7, 2016, 38 pages.
Albrecht et al., "Comparison of roflumilast, a new orally active, selective phosphodiesterase 4 inhibitor, with beclomethasone dipropionate in asthma control," Eur Respir J, 2002, 20 (Suppl 38) 304s.
Anderson, Practical Process Research & Development, Academic Press, 2000, pp. 223-247.
Bayes, et al., "Gateways to Clinical Trials," Oct. 2002, Methods Find Exp Clin Pharmacol 2002, 24(8): 525-552.
Berkow et al., "Obstructive Airway Disease," The Merck Manual, 1997, pp. 173-180.
Bredenbröker et al., "Roflumilast, a new orally active phosphodiesterase 4 inhibitor, is effective in the treatment of chronic obstructive pulmonary disease," Euro. Resp. J. Supp., 2002, 20(Suppl 38): Abst. No. 2330.
Drollmann, A. et. al., "Patients with severe renal impairment do not require dose adjustment of roflumilast," Eur Respir J 2002, 20 (Suppl 38) 108s.

(56) References Cited

OTHER PUBLICATIONS

Federal Register, vol. 65, No. 140 (Jul. 20, 2000), Notices, International Conference on Harmonization; Draft Revised Guidance on Impurities in New Drug Substances.

Fry, Synthetic Organic Electrochemistry, 2nd Edition, John Wiley & Sons, 1989, pp. 17-46.

Guidance for Industry Q3A Impurities in New Drug Substances, Center for Drug Evaluation and Research (CDER) at the Food and Drug Administration ("FDA"), Feb. 2003.

Nassr et al., "Influence of food intake on the pharmacokinetics of roflumilast and its active metabolite roflumilast-N-oxide," Eur J Clin Pharmacol, 2002, 57 (Supp17) S82.

Nassr et al., "No dose adjustment of roflumilast in patients with severe renal impairment," Eur J Clin Pharmacol, 2002, 58 (Supp17) S82.

Poole, "Roflumilast Promising in COPD and Asthma," Inpharma 1364, Nov. 16, 2002.

Schmid-Wirlitsch, et al., "Efficacy and Safety of Once-Daily Roflumilast, A New, Orally Active, Selective Phosphodiesterase 4 Inhibitor, in COPD," National COPD Conference 2003, Arlington, VA, USA, On-Site Program, p. 67.

Timmer et al., "The New Phosphodiesterase 4 Inhibitor Roflumilast is Efficacious in Exercise-Induced Asthma and Leads to Suppression of LPS-Stimulated TNf-α Ex Vivo," The Journal of Clinical Pharmacology, 2002; 42:297-303.

Topliss, "Utilization of Operational Schemesfor Analog Synthesis in Drug Design," J.Med.Chem, 1972, 15(10): 1006-1011.

E.M. Van Schalkwyk, et al., "Dose-dependent inhibitory effect of Roflumilast, a new, orally active, selective phosphodiesterase 4 inhibitor, on allergen-induced early and late asthmatic reaction," ERS 2002, Stockholm, Sweden, Eur Respir J 2002, 20 (Suppl 38) 110s.

Vollhardt and Schore, Organic Chemistry, Structure, and Function, 4th Edition, W.H. Freeman and Co., 2003, pp. 55-58.

Wade, Organic Chemistry, 3rd Edition, 1995, pp. 146-147.

\* cited by examiner

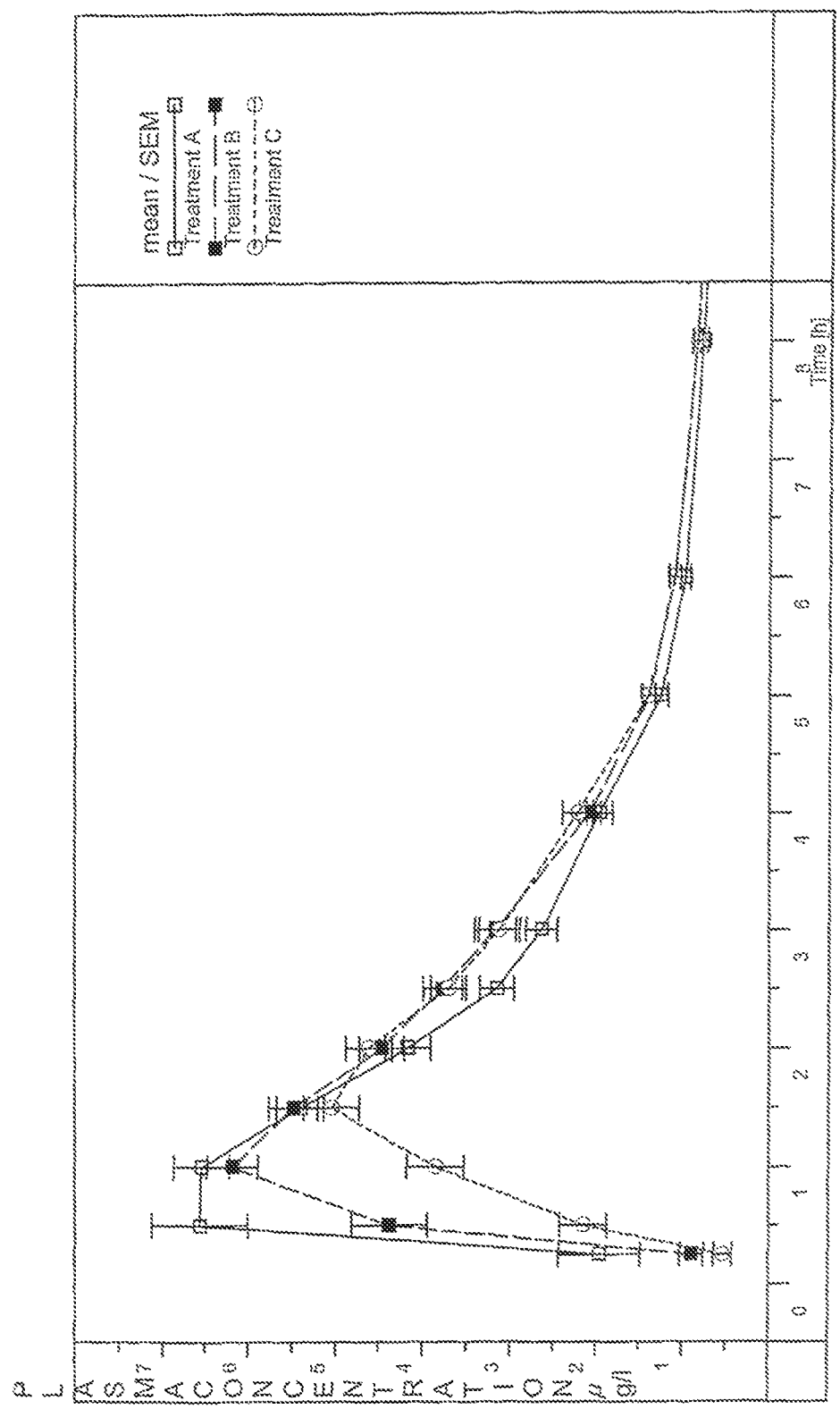

ORAL DOSAGE FORM CONTAINING A PDE 4 INHIBITOR AS AN ACTIVE INGREDIENT AND POLYVINYLPYRROLIDON AS EXCIPIENT

TECHNICAL FIELD

The present invention relates to the field of pharmaceutical technology and describes a dosage form for oral administration of a PDE 4 inhibitor as active ingredient in tablet or pellet form for treating diseases such as asthma or airway obstructions. The invention additionally relates to processes for producing the dosage form.

PRIOR ART

Cyclic nucleotide phosphodiesterase (PDE) inhibitors (specifically of type 4) are currently of special interest as a new generation of active ingredients for treating inflammatory disorders, especially inflammations of the airways such as asthma or airway obstructions (such as, for example, COPD=chronic obstructive pulmonary disease). A number of PDE 4 inhibitors is currently undergoing advanced clinical testing.

In WO00/50011 and WO01/32165, which relate to dosage forms with controlled or sustained delivery of a PDE 4 inhibitor, it is pointed out that unwanted CNS side effects may become manifest on delivery of certain PDE 4 inhibitors such as Ariflo® (INN: cilomilast) in higher dosages. WO00/50011 and WO01/32165 see this as being a particular risk with immediate release dosage forms of the active ingredient and therefore propose administering the PDE 4 inhibitor Ariflo® (INN: cilomilast) in dosage forms with controlled or sustained release.

U.S. Pat. No. 5,286,494 proposes a dosage form with controlled or sustained release for the PDE 4 inhibitor Rolipram whose solubility is slight. However, production of dosage forms with controlled or sustained release of slightly soluble active ingredients may be technically complicated, reference being made thereto for example in U.S. Pat. No. 5,286,494.

The solubility of active ingredients of the PDE 4 inhibitor class in water and aqueous systems may, depending on the chemical structure, be low. Thus, the solubility in water found for the PDE 4 inhibitor N-(3,5-dichloropyrid-4-yl)-3-cyclopropylmethoxy-4-difluoromethoxybenzamide (INN: roflumilast), which is described in WO95/01338, is only 0.53 mg/l at 21° C. The bioavailability of a medicinal substance depends essentially on the release of the medicinal substance from the pharmaceutical form. Faster release and dissolution of the medicinal substance from the formulation means faster absorption thereof. With medicinal substances which are slightly soluble in water, therefore, the bioavailability is frequently limited by the solubility or rate of dissolution. This makes it very difficult to produce suitable dosage forms.

DESCRIPTION OF THE INVENTION

It is an object of the present invention to provide a dosage form for oral administration of PDE 4 inhibitors whose solubility is slight, which form can be produced without great technical complexity, which takes account of the low solubility of the PDE 4 inhibitor whose solubility is slight, and which results in rapid, acceptable bioavailability of the PDE 4 inhibitor whose solubility is slight, so as to attain serum levels which are required in order to obtain the desired pharmacological effect quickly without side effects becoming manifest.

It has now been found, surprisingly, that this object can be achieved by a dosage form for oral administration of a PDE 4 inhibitor whose solubility is slight, employing polyvinylpyrrolidone (PVP) as binder for the dosage form. Compared with dosage forms in which no PVP is employed as binder, the dosage form of the invention shows distinctly improved pharmacokinetic properties. Thus, in particular in relation to the bioavailability of the PDE 4 inhibitor whose solubility is slight, a faster absorption and thus faster onset of the pharmacological effect is observed with the dosage forms of the invention compared with dosage forms without PVP. The oral dosage form of the invention is preferably a solid dosage form in tablet or pellet form. It is preferably a solid oral dosage form with immediate release of the active ingredient (immediate release solid oral dosage form).

The invention therefore relates to a dosage form in tablet or pellet form for oral administration of a PDE 4 inhibitor whose solubility is slight, comprising the PDE 4 inhibitor whose solubility is slight together with polyvinylpyrrolidone as binder, and one or more other suitable pharmaceutical excipients.

The PDE 4 inhibitor whose solubility is slight is preferably according to the invention a compound from the group of compounds of the formula I

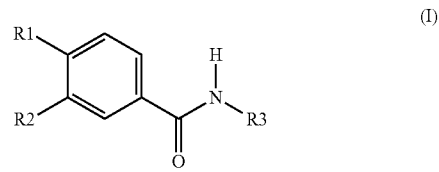

in which either
R1 is 3-7C cycloalkoxy, 3-7C cycloalkylmethoxy or benzyloxy and
R2 is 1-4C alkoxy which is completely or partly substituted by fluorine,
or
R1 is 1-4C alkoxy which is completely or partly substituted by fluorine and
R2 is 3-7C cycloalkylmethoxy or benzyloxy,
and
R3 is phenyl, pyridyl, phenyl substituted by R31, R32 and R33, or pyridyl substituted by R34, R35, R36 and R37, where
R31 is hydroxyl, halogen, cyano, carboxyl, trifluoromethyl, 1-4C alkyl, 1-4C alkoxy, 1-4C alkoxy-carbonyl, 1-4C alkylcarbonyl, 1-4C alkylcarbonyloxy, amino, mono- or di-1-4C alkylamino or 1-4C alkylcarbonylamino,
R32 is hydrogen, hydroxyl, halogen, amino, trifluoromethyl, 1-4C alkyl or 1-4C alkoxy,
R33 is hydrogen, halogen, 1-4C alkyl or 1-4C alkoxy,
R34 is hydroxyl, halogen, cyano, carboxyl, 1-4C alkyl, 1-4C alkoxy, 1-4C alkoxycarbonyl or amino,
R35 is hydrogen, halogen, amino or 1-4C alkyl,
R36 is hydrogen or halogen and
R37 is hydrogen or halogen,
the salts of these compounds and the N-oxides of the pyridines and the salts thereof.

3-7C Cycloalkoxy is, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C Cycloalkylmethoxy is, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Examples which may be mentioned of 1-4C alkoxy which is completely or partly substituted by fluorine are 1,2,2-trifluoroethoxy, 2,2,3,3,3-pentafluoropropoxy, perfluoroethoxy and, in particular, 1,1,2,2-tetra-fluoroethoxy, trifluoromethoxy, 2,2,2-trifluoroethoxy and difluoromethoxy radicals.

Halogen for the purposes of the present invention is bromine, chlorine and fluorine.

1-4C Alkyl represents straight-chain or branched alkyl radicals having 1 to 4 carbon atoms. Examples which may be mentioned are butyl, isobutyl, sec-butyl, tert-butyl, propyl, isopropyl, ethyl and methyl radicals.

1-4C Alkoxy is a radical which, besides the oxygen atom, contains one of the aforementioned 1-4C alkyl radicals. Examples which may be mentioned are the methoxy and ethoxy radicals.

1-4C Alkoxycarbonyl is a carbonyl group to which one of the aforementioned 1-4C alkoxy radicals is bonded. Examples which may be mentioned are the methoxycarbonyl ($CH_3O-CO-$) and ethoxycarbonyl ($CH_3CH_2O-CO-$) radicals.

1-4C Alkylcarbonyl is a carbonyl group to which one of the aforementioned 1-4C alkyl radicals is bonded. An example which may be mentioned is the acetyl radical ($CH_3CO-$).

1-4C Alkylcarbonyloxy radicals comprise besides the oxygen atom one of the aforementioned 1-4C alkylcarbonyl radicals. An example which may be mentioned is the acetoxy radical ($CH_3CO-O-$).

Examples of mono- or di-1-4C alkylamino radicals which may be mentioned are the methylamino, dimethylamino and diethylamino radicals.

An example of a 1-4C alkylcarbonylamino radical which may be mentioned is the acetylamino radical ($-NH-CO-CH_3$).

Examples of phenyl radicals substituted by R31, R32 and R33 which may be mentioned are the radicals 2-acetylphenyl, 2-aminophenyl, 2-bromophenyl, 2-chlorophenyl, 2,3-dichlorophenyl, 2,4-dichlorophenyl, 4-diethylamino-2-methylphenyl, 4-bromo-2-trifluoromethylphenyl, 2-carboxy-5-chlorophenyl, 3,5-dichloro-2-hydroxyphenyl, 2-bromo-4-carboxy-5-hydroxyphenyl, 2,6-dichlorophenyl, 2,5-dichlorophenyl, 2,4,6-trichlorophenyl, 2,4,6-trifluorophenyl, 2,6-dibromophenyl, 2-cyanophenyl, 4-cyano-2-fluorophenyl, 2-fluorophenyl, 2,4-difluorophenyl, 2,6-difluorophenyl, 2-chloro-6-fluorophenyl, 2-hydroxyphenyl, 2-hydroxy-4-methoxyphenyl, 2,4-dihydroxyphenyl, 2-methoxyphenyl, 2,3-dimethoxy-phenyl, 2,4-dimethoxyphenyl, 2,6-dimethoxyphenyl, 2-dimethylaminophenyl, 2-methylphenyl, 2-chloro-6-methylphenyl, 2,4-dimethylphenyl, 2,6-dimethylphenyl, 2,3-dimethylphenyl, 2-methoxycarbonylphenyl, 2-trifluoromethylphenyl, 2,6-dichloro-4-methoxyphenyl, 2,6-dichloro-4-cyanophenyl, 2,6-dichloro-4-aminophenyl, 2,6-dichloro-4-methoxycarbonylphenyl, 4-acetylamino-2,6-dichlorophenyl and 2,6-dichloro-4-ethoxycarbonylphenyl.

Examples of pyridyl radicals substituted by R34, R35, R36 and R37 which may be mentioned are the radicals 3,5-dichloropyrid-4-yl, 2,6-diaminopyrid-3-yl, 4-aminopyrid-3-yl, 3-methylpyrid-2-yl, 4-methylpyrid-2-yl, 5-hydroxypyrid-2-yl, 4-chloropyrid-3-yl, 3-chloropyrid-2-yl, 3-chloropyrid-4-yl, 2-chloropyrid-3-yl, 2,3,5,6-tetrafluoropyrid-4-yl, 3,5-dichloro-2,6-difluoropyrid-4-yl, 3,5-dibromopyrid-2-yl, 3,5-dibromopyrid-4-yl, 3,5-dichloropyrid-4-yl, 2,6-dichloropyrid-3-yl, 3,5-dimethylpyrid-4-yl, 3-chloro-2,5,6-trlfluoropyrid-4-yl and 2,3,5-trifluoropyrid-4-yl.

Salts suitable for compounds of the formula I—depending on the substitution—are all acid addition salts but, in particular, all salts with bases. Particular mention may be made of the pharmacologically acceptable salts of the inorganic and organic acids and bases normally used in pharmaceutical technology. Pharmacologically unacceptable salts which, for example, may be the initial products of the process for preparing the compounds of the invention on the industrial scale are converted into pharmacologically acceptable salts by processes known to the skilled worker. Those suitable on the one hand are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid, or 3-hydroxy-2-naphthoic acid, the acids being employed to prepare the salts in the equimolar ratio of amounts, or one differing therefrom—depending on whether the acid is monobasic or polybasic and depending on which salt is desired.

On the other hand, salts with bases are also particularly suitable. Examples of basic salts which may be mentioned are lithium, sodium, potassium, calcium, aluminum, magnesium, titanium, ammonium, meglumine or guanidinium salts, once again the bases being employed to prepare the salts in the equimolar ratio of amounts or one differing therefrom.

Compounds of the formula I to be emphasized are those in which either

R1 is 3-5C cycloalkoxy, 3-5C cycloalkylmethoxy or benzyloxy and

R2 is 1-4C alkoxy which is completely or partly substituted by fluorine, or

R1 is 1-4C alkoxy which is completely or partly substituted by fluorine and

R2 is 3-5C cycloalkylmethoxy or benzyloxy, and

R3 is phenyl, pyridyl, phenyl substituted by R31, R32 and R33, or pyridyl substituted by R34, R35, R36 and R37, where R31 is halogen, cyano, carboxyl, 1-4C alkyl, 1-4C alkoxy or 1-4C alkoxycarbonyl, R32 is hydrogen, halogen, 1-4C alkyl or 1-4C alkoxy, R33 is hydrogen, halogen, 1-4C alkyl or 1-4C alkoxy, R34 is halogen or 1-4C alkyl, R35 is hydrogen or halogen, R36 is hydrogen or halogen and R37 is hydrogen or halogen, the salts of these compounds, and the N-oxides of the pyridines and salts thereof.

Compounds of the formula I to be particularly emphasized are those in which either
R1 is 3-5C cycloalkoxy, 3-5C cycloalkylmethoxy or benzyloxy and
R2 is 1-4C alkoxy which is completely or partly substituted by fluorine,
Or
R1 is 1-4C alkoxy which is completely or partly substituted by fluorine and
R2 is 3-5C cycloalkylmethoxy or benzyloxy and
R3 is 2-bromophenyl, 2,6-dichloro-4-ethoxycarbonylphenyl, 2,6-dimethoxyphenyl, 4-cyano-2-fluoro-phenyl, 2,4,6-trifluorophenyl, 2-chloro-6-methylphenyl, 2,6-dimethylphenyl, 2,6-difluorophenyl, 2,6-dichlorophenyl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
the salts of these compounds, and the N-oxides of the pyridines and salts thereof.

Preferred compounds of the formula I are those in which
R1 is difluoromethoxy,
R2 is cyclopropylmethoxy and
R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluoro-phenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
the salts of these compounds, and the N-oxides of the pyridines and salts thereof.

A particularly preferred compound of the formula I is the one in which
R1 is difluoromethoxy,
R2 is cyclopropylmethoxy and
R3 is 3,5-dichloropyrid-4-yl,
the salts of these compounds, and the N-oxide of the pyridine and salts thereof.

This compound has the chemical name N-(3,5-dichloropyrid-4-yl)-3-cyclopropylmethoxy-4-difluoromethoxybenzamide (INN: roflumilast).

The PDE 4 inhibitor whose solubility is slight is preferably a PDE 4 inhibitor with a solubility in water of less than or equal to 100 milligram/liter, particularly preferably with a solubility in water of less than or equal to 1 milligram/liter, at a temperature of 15 to 25° C., in particular at 21° C. This compound is particularly preferably one of the formula I.

The abovementioned compounds of the formula I and the use of these compounds as phosphodiesterase (PDE) 4 inhibitors are described in the international patent application WO95/01338.

Further suitable pharmaceutical excipients which may be used in the dosage form of the invention are pharmaceutical excipients such as fillers, additional binders, tablet disintegrants or else lubricants and release agents. Other suitable excipients which may be present in the dosage form of the invention are, for example, flavoring substances (such as flavors and sweeteners), buffer substances, preservatives, coloring substances (such as iron oxid yellow or red) or else emulsifiers. Flavors are usually added in a proportion of from 0.05 to 1% by weight. Other flavoring substances by way of example are acids such as citric acid, sweeteners such as saccharin, aspartame, cyclamate sodium or maltol, which are added according to the desired result.

The polyvinylpyrrolidone (PVP) employed according to the invention is, in particular, a water-soluble PVP with an average molecular weight above 2 000, preferably above 20 000. Examples which may be mentioned are Kollidon 12 PF (molecular weight 2 000-3 000), Kollidon 17 PF (molecular weight 7 000-11 000), Kollidon 25 (molecular weight 28 000-34 000), Kollidon 30 (molecular weight 44 000-54 000), Kollidon 90 F (molecular weight 1 000 000-1 500 000). PVP of higher molecular weight such as, for example, Kollidon 25, Kollidon 30 and Kollidon 90 F may be mentioned as preferred.

It is possible if desired to employ in addition to PVP other binders such as polyvinyl acetate (e.g. Kollidon® VA 64), gelatin, corn starch mucilage, preswollen starches (Starch 1500), hydroxypropyl-methylcellulose (HPMC) or hydroxypropylcellulose (L-HPC).

Fillers suitable according to the invention are fillers such as calcium carbonate (e.g. MagGran® CC or Destab® 95) and sodium carbonate, sugar alcohols such as mannitol (e.g. Perlitol® or Parteck® M), sorbitol (e.g. Karlon®), xylitol or maltitol, starches such as corn starch, potato starch and wheat starch, microcrystalline cellulose, saccharides such as glucose, lactose (e.g. lactose monohydrate), levulose, sucrose and dextrose. It is also possible if desired to use mixtures thereof. Corn starch, microcrystalline cellulose and lactose may be mentioned as preferred.

Examples of suitable lubricants and release agents which may be mentioned are sodium stearyl fumarate, magnesium stearate, calcium stearate, stearic acid, talc and colloidal anhydrous silica (Aerosil).

Disintegrants suitable according to the invention are, in particular, insoluble polyvinylpyrrolidone (Insoluble PVP, crospovidone), carboxymethylstarch sodium [=sodium starch glycolate], sodium carboxymethylcellulose, alginic acid, and starches able to carry out the function of a disintegrant (e.g. Starch 1500).

The proportion (in percent by weight based on the finished dosage form) of PDE 4 inhibitor in the dosage form of the invention is usually, depending on the nature of the PDE 4 inhibitor, from 0.01 to 50% by weight. The proportion of PDE 4 inhibitor is preferably up to 20% by weight.

The proportion (in percent by weight based on the finished dosage form) of binder (PVP and, where appropriate, other binders) may preferably be according to the invention from 0.5 to 20% by weight. The proportion of PVP is preferably from 1 to 5% by weight, particularly preferably 2 to 3% by weight.

The proportion (in percent by weight based on the finished dosage form) of filler in the tablet of the invention is advantageously from 40 to 99% by weight. The proportion of filler is preferably from 60 to 97% by weight.

The proportion (in percent by weight based on the finished dosage form) of disintegrant in the rapidly disintegrating tablet can usually be up to 35% by weight. The proportion of disintegrant is preferably from 2 to 20% by weight. The proportion of disintegrant is particularly preferably from 5 to 10% by weight.

The proportion (in percent by weight based on the finished dosage form) of lubricant or release agent in the rapidly disintegrating tablet is usually from 0.1 to 5% by weight. The proportion of lubricant or release agent is preferably from 0.3 to 3% by weight. The proportion of lubricant or release agent is particularly preferably from 0.5 to 2% by weight.

In a preferred embodiment of the invention, the dosage form is a tablet. It is preferred for the tablet, besides the PDE 4 inhibitor whose solubility is slight and PVP, to comprise as further pharmaceutical excipients at least one filler and at least one lubricant or release agent.

The pharmaceutical preparation of the invention can be produced by processes known to the skilled worker for producing tablets and pellets.

In one embodiment of the invention, the pharmaceutical form of the invention is produced by producing a solid solution of the PDE 4 inhibitor whose solubility is slight in the binder PVP as carrier. This can take place for example by the solvent method in which PVP, the PDE 4 inhibitor and, where appropriate, other pharmaceutical excipients are dissolved in a suitable solvent, and the solvent is subsequently removed again by spray drying, normal drying, vacuum drying or freeze-drying. It has been found, surprisingly, that production of the solid solution is also possible by the mixing method in which a PDE 4 inhibitor whose solubility is slight and, where appropriate, other pharmaceutical excipients are vigorously mixed together with PVP.

The invention also relates further to a solid solution of a PDE 4 inhibitor whose solubility is slight in the binder PVP as carrier. A solid solution of the PDE 4 inhibitor in the binder PVP as carrier means according to the invention a solid solution with amorphous structure in which the PDE 4 inhibitor is in the form of a molecular dispersion in the carrier material.

In the event of further processing of a solid solution to tablets or pellets, the solid solution may be processed as active ingredient component together with the filler, binder, disintegrant and lubricant components by production processes familiar to the skilled worker to give the oral dosage forms of the invention.

The invention therefore also relates to a process for producing a dosage form in tablet or pellet forms for oral administration of a PDE 4 inhibitor, comprising the steps: (a) production of an active ingredient preparation in the form of a solid solution in PVP of the PDE 4 inhibitor whose solubility is slight, (b) production of a mixture of an active ingredient preparation and pharmaceutical excipients and (c) granulation of the mixture obtained in (b) with an aqueous solution of PVP.

In the case of dosage forms of the invention in the form of tablets, the granules obtained in (c) can, after drying and mixing with lubricants or release agents, be compressed in a tablet press. In the case of dosage forms of the invention in the form of pellets, the wet granules obtained in (c) can be processed by the extruder/spheroidizer process to suitable pellets. Alternatively, dispersions/suspensions of an active ingredient preparation can be applied in the form of a solid solution in PVP of the PDE 4 inhibitor whose solubility is slight in a suitable solvent to pellet-like carriers (e.g. nonpareils or HPMC-containing pellets).

In another preferred embodiment of the invention, the dosage form of the invention is produced by granulating a mixture of active ingredient and pharmaceutical excipients with an aqueous PVP solution, drying the granules and, if desired, admixing other pharmaceutical excipients. Wet preparations obtained after granulation can then be further processed to pellets and can subsequently be packed into capsules. Dried granules can—if desired after admixture of other pharmaceutical excipients—after mixing with a release agent be compressed in a tablet press. The granulation preferably takes place in a fluidized bed granulator under suitable conditions. It is moreover possible if desired for the active ingredient to be admixed to the other pharmaceutical excipients in the form of a trituration with a pharmaceutical excipient (especially a filler). This is particularly preferred when the active ingredient content in the dosage form is less than 5% by weight. Such a trituration can normally be obtained by grinding the active ingredient with a pharmaceutical excipient (especially a filler).

The invention therefore also relates to a process for producing a dosage form in tablet or pellet form for oral administration of a PDE 4 inhibitor comprising the steps:
(a) production of a mixture of active ingredient and pharmaceutical excipients and
(b) granulation of the mixture obtained in (a) with an aqueous solution of PVP.

The dosage form of the invention is particularly preferably produced by granulation of a mixture of
(a) PDE 4 inhibitor whose solubility is slight, or a trituration of the PDE 4 inhibitor whose solubility is slight with corn starch,
(b) corn starch and
(c) lactose monohydrate
with an aqueous PVP solution, drying of the granules, mixing of the granules with a release agent and compression in a tablet press. The PDE 4 inhibitor whose solubility is slight is in this case particularly preferably roflumilast, the salts thereof, the N-oxide of the pyridine and salts thereof.

Alternatively, the dosage form of the invention is particularly preferably produced by granulation of a mixture of
(a) PDE 4 inhibitor whose solubility is slight, or a trituration of the PDE 4 inhibitor whose solubility is slight with corn starch,
(b) corn starch,
(c) microcrystalline cellulose and
(d) sodium carboxymethylstarch
with an aqueous PVP solution, drying of the granules, mixing of the granules with a release agent and compression in a tablet press. The PDE 4 inhibitor whose solubility is slight is in this case particularly preferably roflumilast, the salts thereof, the N-oxide of the pyridine and salts thereof.

In a further preferred embodiment of the invention, the dosage form of the invention is produced by granulation of a mixture of pharmaceutical excipients with a suspension of the active ingredient in an aqueous PVP solution, drying of the granules and, if desired, admixture of further pharmaceutical excipients. The preparations obtained in this way can then, after mixing with a release agent, be compressed in a tablet press. The granulation preferably takes place in a fluidized bed granulator under suitable conditions.

The invention therefore also relates to a process for producing a dosage form in tablet or pellet form for oral administration of a PDE 4 inhibitor comprising the steps:
(a) production of a mixture of pharmaceutical excipients and
(b) granulation of the mixture obtained in (a) with a suspension of the active ingredient in an aqueous solution of PVP.

The dosage form of the invention is particularly preferably produced by granulation of a mixture of corn starch and lactose monohydrate with a suspension of the PDE 4 inhibitor whose solubility is slight in an aqueous solution of PVP, drying of the granules, mixing of the granules with a release agent and compression in a tablet press.

It has surprisingly been found that dosage forms of the invention produced employing physical mixtures or triturations of the PDE 4 inhibitor whose solubility is slight with a filler (e.g. by grinding, vigorous mixing or extrusion) and subsequent granulation with aqueous PVP solutions, or produced employing granulation suspensions of PDE 4 inhibitors in aqueous PVP solutions, have similar advantageous properties in relation to the bioavailability of the PDE 4 inhibitor whose solubility is slight as do dosage forms produced by first producing solid solutions of PVP and PDE 4 inhibitor. This suggests that in the production of the dosage forms of the invention based on physical mixtures or triturations of the PDE 4 inhibitor whose solubility is slight with a filler, which are subsequently granulated with aqueous PVP solutions, or in whose preparation granulation suspensions of PDE 4 inhibitors in aqueous PVP solutions are employed, there are, surprisingly, interactions between PVP and PDE 4 inhibitor whose solubility is slight, like those occurring in the solid solution of PVP and PDE 4 inhibitor. In the production of the dosage forms of the invention it is therefore also possible to dispense with the more technically elaborate variant of production of a solid solution by the solvent method.

DESCRIPTION OF THE FIGURE

FIG. 1 shows the time course of the average serum concentration of roflumilast after oral administration of 0.5 mg (2 tablets each containing 0.25 mg) of roflumilast from dosage forms of the invention compared with a dosage form containing no PVP.

The production of tablets and preparations of the invention is described by way of example below. The following examples explain the invention in more detail without restricting it.

EXAMPLES

Production of Tablets of the Invention

Example A

Weight Based on a Tablet Containing 0.1 mg of Roflumilast

| 1. | Roflumilast (micronized) | 0.100 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
|    | Total | 65.100 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.1 mg.

Example B

Weight Based on a Tablet Containing 0.125 mg of Roflumilast

| 1. | Roflumilast | 0.125 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
|    | Total | 65.125 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.125 mg.

Example C

Weight Based on a Tablet Containing 0.25 mg of Roflumilast

| 1. | Roflumilast | 0.250 mg |
| 2. | Microcrystalline cellulose | 33.900 mg |
| 3. | Corn starch | 2.500 mg |
| 4. | Polyvidone K90 | 2.250 mg |
| 5. | Sodium carboxymethylstarch (type A) | 20.000 mg |
| 6. | Magnesium stearate (vegetable) | 0.600 mg |
|    | Total | 59.500 mg |

Production: (1) is mixed with part of (3), and a trituration is produced in a planetary mill. The trituration is put together with (2), (5) and the remaining amount of (3) in the product container of a fluidized bed granulation system, and a 5% granulation solution of (4) in purified water is sprayed on and dried under suitable conditions. (6) is added to the granules, and the mixture obtained after mixing is compressed in a tablet press to tablets having an average weight of 59.5 mg.

Example D

Weight Based on a Tablet Containing 0.25 mg of Roflumilast

| 1. | Roflumilast | 0.250 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
|    | Total | 65.250 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.25 mg.

Example E

Weight Based on a Tablet Containing 0.5 mg of Roflumilast

| 1. | Roflumilast | 0.500 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
|    | Total | 65.500 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.500 mg.

Example F

Weight Based on a Tablet Containing 0.5 mg of Roflumilast

| 1. | Roflumilast | 0.500 mg |
|---|---|---|
| 2. | Lactose monohydrate | 99.320 mg |
| 3. | Corn starch | 26.780 mg |
| 4. | Polyvidone K90 | 2.600 mg |
| 5. | Magnesium stearate (vegetable) | 1.300 mg |
| | Total | 130.500 mg |

Production: (1) is mixed with part (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 130.5 mg.

Example G

Weight Based on a Tablet Containing 2.5 mg of Roflumilast

| 1. | Roflumilast | 2.500 mg |
|---|---|---|
| 2. | Microcrystalline cellulose | 33.900 mg |
| 3. | Corn starch | 2.500 mg |
| 4. | Polyvidone K90 | 2.250 mg |
| 5. | Sodium carboxymethylstarch (type A) | 20.000 mg |
| 6. | Magnesium stearate (vegetable) | 0.600 mg |
| | Total | 61.750 mg |

Production: (1) is mixed with part of (3), and a trituration is produced in a planetary mill. The trituration is put together with (2), (5) and the remaining amount of (3) in the product container of a fluidized bed granulation system, and a 5% granulation solution of (4) in purified water is sprayed on and dried under suitable conditions. (6) is added to the granules, and the mixture obtained after mixing is compressed in a tablet press to tablets having an average weight of 61.75 mg.

Example H

Production of Tablets Containing 0.1 mg of Roflumilast as Active Ingredient (Weight for a Batch of 70 000 Tablets)

| 1. | Roflumilast (micronized) | 7.000 g |
|---|---|---|
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4557.000 g |

Production: (1) is mixed with 70 g of (3), and a trituration is produced in a planetary mill. The trituration is put together with (2) and the remaining amount of (3) in the product container of a fluidized bed granulation system, and a 5% granulation solution of (4) in purified water is sprayed on. (Spraying pressure: 3 bar; product temperature: 28-33° C.; air flow rate in the first third of the spraying process: 100 m³/h; air flow rate subsequently during the spraying process: 150 m³/h; inlet air temperature: 40-70° C.; spraying rate: 30-40 g/min). After spraying is complete, drying is carried out until the product temperature reaches 34° C. The granules are passed through a stainless steel sieve with a mesh width of 0.8 mm, and the relative surface moisture is measured and adjusted to a value in the range 20-50%. (5) is added to the granules, and the mixture obtained after mixing is compressed in a tablet press to tablets having an average weight of 65.1 mg.

Example I

Production of Tablets Containing 0.25 mg of Roflumilast as Active Ingredient (Weight for a Batch of 70 000 Tablets)

| 1. | Roflumilast (micronized) | 35.000 g |
|---|---|---|
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4585.000 g |

Production: 19:25 g of (1) are mixed with 192.5 g of (3), and a trituration is produced in a planetary mill. The trituration is put together with (2) and the remaining amount of (3) in the product container of a fluidized bed granulation system, and a 5% granulation solution of (4) in purified water is sprayed on. (Spraying pressure: 3 bar, product temperature: 28-33° C.; air flow rate in the first third of the spraying process: 100 m³/h; air flow rate subsequently during the spraying process: 150 m³/h; inlet air temperature: 40-70° C.; spraying rate: 30-40 g/min). After spraying is complete, drying is carried out until the product temperature reaches 34° C. The granules are passed through a stainless steel sieve with a mesh width of 0.8 mm, and the relative surface moisture is measured and adjusted to a value in the range 20-50%. (5) is added to the granules, and the mixture obtained after mixing is compressed in a tablet press to tablets having an average weight of 65.5 mg.

Example J

Production of Tablets Containing 0.1 mg of Roflumilast as Active Ingredient (Weight for a Batch of 70 000 Tablets)

| 1. | Roflumilast (micronized) | 7.000 g |
|---|---|---|
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4557.000 g |

Production: (1) is homogeneously suspended in a granulation solution of (4) in purified water. (2) and (3) are put into the product container of a suitable fluidized bed granulation system and granulated with the granulation suspension described above, and then dried. (5) is added to the granules, and the mixture obtained after mixing is compressed in a tablet press to tablets having an average weight of 65.1 mg.

Example K

Production of Tablets Containing 0.25 mg of Roflumilast as Active Ingredient (Weight for a Batch of 70 000 Tablets)

| 1. | Roflumilast (micronized) | 35.000 g |
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4585.000 g |

Production: (1) is homogeneously suspended in a granulation solution of (4) in purified water. (2) and (3) are put into the product container of a suitable fluidized bed granulation system and granulated with the granulation suspension described above, and then dried. (5) is added to the granules, and the mixture obtained after mixing is compressed in a tablet press to tablets having an average weight of 65.25 mg.

Example L

Weight Based on a Tablet Containing 0.25 mg of Roflumilast

| 1. | Roflumilast | 0.250 mg |
| 2. | Lactose monohydrate | 49.660 mg |
| 3. | Potato starch | 10.000 mg |
| 4. | Corn starch | 3.590 mg |
| 5. | PVP 25 | 1.500 mg |
| 6. | Magnesium stearate (vegetable) | 0.650 mg |
| | Total | 65.650 mg |

Production: A dispersion is produced from (4) and water, and (1) is homogeneously suspended therein. (5) is dissolved in water and added to the dispersion. (2) and (3) are granulated in a suitable fluidized bed granulation system with the dispersion under suitable conditions. (6) is added to this mixture, and the mixture obtained after mixing is compressed in a tablet press to tablets having an average weight of 65.650 mg.

Example M

Weight Based on a Tablet Containing 0.25 mg of Roflumilast

| 1. | Roflumilast | 0.250 mg |
| 2. | Lactose monohydrate | 49.660 mg |
| 3. | Corn starch | 13.390 mg |
| 4. | Polyvidone K90 | 1.300 mg |
| 5. | Gelatin | 1.300 mg |
| 6. | Magnesium stearate (vegetable) | 0.650 mg |
| | Total | 66.550 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) and (5) in purified water is sprayed on and dried under suitable conditions. (6) is added to the granules, and the mixture obtained after mixing is compressed in a tablet press to tablets having an average weight of 66.55 mg.

Example M1

Formulation for Pediatric Use
Weight Based on a Tablet Containing 0.125 mg of Roflumilast

| 1. | Roflumilast | 0.125 mg |
| 2. | Lactose monohydrate | 49.660 mg |
| 3. | Corn starch | 13.390 mg |
| 4. | Polyvidone K90 | 1.300 mg |
| 5. | Mannit | 32.238 mg |
| 6. | Flavor (Tutti Frutti) | 0.329 mg |
| 7. | PVP (Insoluble) | 12.895 mg |
| 5. | Magnesium stearate (vegetable) | 1.649 mg |
| | Total | 111.586 mg |

The formulation is produced according to a process disclosed above.
Physical Investigations and Comparative Tests with Dosage Forms in which no PVP was Used as Binder Example N The disintegration time and the release of active ingredient were determined for a dosage form corresponding to example D.

Disintegration time: the disintegration time was determined using a disintegration tester by the method described in the European Pharmacopoeia.
Result: 7.08 minutes.
Release of active ingredient: the release of active ingredient was determined as described in the US Pharmacopeia (USP XXV; apparatus 2).
Result: 78% of the active ingredient are released after 15 minutes, and quantitative release is observed after 60 minutes.

Example O

Production of a Dosage Form Containing Roflumilast in which No PVP is Used:
Weight Based on a Tablet Containing 0.25 mg of Roflumilast

| 1. | Roflumilast | 0.250 mg |
| 2. | Lactose monohydrate | 70.300 mg |
| 3. | Potato starch | 19.475 mg |
| 4. | Corn starch | 3.563 mg |
| 5. | Sodium carboxymethytstarch (Type A) | 1.900 mg |
| 6. | Magnesium stearate (vegetable) | 0.950 mg |
| | Total | 96.438 mg |

Production: A dispersion is produced from (4) and water, and (1) is homogeneously suspended therein. (2) and (3) are granulated in a suitable fluidized bed granulation system with the dispersion under suitable conditions. (5) is added to the dry granules, and a homogeneous mixture is produced. (5) is added to this mixture, and the mixture obtained after mixing is compressed in a tablet press to tablets having an average weight of 96.438 mg.
Comparative Study
Design: 24 subjects, 3-period changeover, randomized; dose in each case 0.5 mg (2 tablets each containing 0.25 mg of roflumilast). The serum concentration of roflumilast after oral administration of 0.5 mg (2 tablets each containing 0.25 mg) of roflumilast was investigated for the following dosage forms:

With PVP as Binder.

Tablet corresponding to example D, referred to as "treatment A" hereinafter.

Tablet corresponding to example K, referred to as "treatment B" hereinafter.

Without PVP as Binder:

Tablet corresponding to example O, referred to as "treatment C" hereinafter.

The results are depicted in FIG. 1. Higher serum levels were observed considerably more quickly after oral administration for dosage forms with PVP as binder compared with dosage forms without PVP. The rate of absorption is thus distinctly increased for the dosage forms of the invention.

Industrial Applicability

The dosage forms of the invention can be employed for the treatment and prevention of all diseases regarded as treatable or preventable through the use of PDE 4 inhibitors. Selective cyclic nucleotide phosphodiesterase (PDE) inhibitors (specifically of type 4) are suitable on the one hand as bronchial therapeutic agents (for the treatment of airway obstructions owing to their dilating effect but also owing to their effect increasing the respiratory rate and respiratory drive) and for eliminating erectile dysfunction owing to the vasodilating effect, but on the other hand especially for the treatment of disorders, especially of an inflammatory nature, e.g. of the airways (asthma prophylaxis), of the skin, of the central nervous system, of the intestine, of the eyes and of the joints, which are promoted by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. The pharmaceutical preparations of the invention can therefore be used in human and veterinary medicine for example for the treatment and prophylaxis of the following diseases: acute and chronic (especially inflammatory and allergen-induced) airway disorders of various etiologies (bronchitis, allergic bronchitis, bronchial asthma, COPD); dermatoses (especially of a proliferative, inflammatory and allergic nature) such as, for example, psoriasis (vulgaris), toxic and allergic contact eczema, atopic eczema, seborrhoic eczema, lichen simplex, sunburn, pruritus in the genitoanal region, alopecia areata, hypertrophic scars, discoid lupus erythematosus, follicular and extensive pyodermas, endogenous and exogenous acne, acne rosacea and other proliferative, inflammatory and allergic skin disorders; disorders based on excessive release of TNF an leukotrienes, e.g. disorders of the arthritic type (rheumatoid arthritis, rheumatoid spondylitis, osteoarthritis and other arthritic states), disorders of the immune system (AIDS, multiple sclerosis), types of shock [septic shock, endotoxin shock, gram-negative sepsis, toxic shock syndrome and ARDS (adult respiratory distress syndrome)] and generalized inflammations in the gastrointestinal region (Crohn's disease and ulcerative colitis); disorders based on allergic and/or chronic abnormal immunological reactions in the region of the upper airways (pharyngeal space, nose) and adjacent regions (paranasal sinuses, eyes), such as, for example, allergic rhinitis/sinusitis, chronic rhinitis/sinusitis, allergic conjunctivitis and nasal polyps; but also cardiac disorders which can be treated by PDE inhibitors, such as, for example, heart failure, or disorders which can be treated owing to the tissue-relaxant effect of PDE inhibitors, such as, for example, erectile dysfunction or colic of the kidneys and ureters connected with kidney stones; or else disorders of the CNS such as, for example, depressions or arteriosclerotic dementia.

The invention further relates to a method for the treatment of mammals, including humans, suffering from one of the abovementioned diseases. The method is characterized by administration of a therapeutically effective and pharmacologically suitable amount of a PDE 4 inhibitor to the mammalian patient, the PDE 4 inhibitor being present in a dosage form of the invention. The disease is preferably asthma or airway obstructions, especially COPD (=chronic obstructive pulmonary disease).

The dosage forms of the invention comprise the PDE 4 inhibitor in the dose customary for the treatment of the particular disease. The dosage of the active ingredient is of the order of magnitude customary for PDE inhibitors, it being possible to administer the daily dose in one or more dosage units. The normal dose on systemic therapy (oral) is between 0.001 mg and 3 mg per kilogram and day. Dosage forms preferred according to the invention contain from 0.01 mg to 5 mg of roflumilast, preferably from 0.05 mg to 2.5 mg, particularly preferably 0.1 mg to 0.5 mg of roflumilast per dosage unit. Examples of pharmaceutical preparations of the invention contain 0.1 mg, 0.125 mg, 0.25 mg and 0.5 mg of roflumilast per dosage unit. Normally, one or more than one dosage unit of the invention is administered once a day. If desired, it is also possible for one or more dosage units of the invention to be administered more than once a day.

The invention claimed is:

1. A solid dosage form in tablet or pellet form for the oral administration of roflumilast, comprising: roflumilast—0.250 mg; lactose monohydrate—49.660 mg; corn starch—13.390 mg; polyvinylpyrrolidone having a weight average molecular weight of between 1,000,000 and 1,500,000-1.300 mg; and magnesium stearate—0.650 mg and wherein said dosage form provides immediate release of said roflumilast.

2. A solid dosage form in tablet or pellet form for the oral administration of roflumilast, comprising: roflumilast—0.500 mg; lactose monohydrate—49.660 mg; corn starch—13.390 mg; polyvinylpyrrolidone having a weight average molecular weight of between 1,000,000 and 1,500,000-1.300 mg; and magnesium stearate—0.650 mg and wherein said dosage form provides immediate release of said roflumilast.

3. The dosage form according to claim 1, wherein the dosage form is a tablet.

4. The dosage form according to claim 2, wherein the dosage form is a tablet.

5. A pharmaceutical dosage form, comprising a tablet of 0.500 mg roflumilast; 49.660 mg lactose monohydrate; 13.390 mg corn starch; 1.300 mg polyvinylpyrrolidone having a weight average molecular weight of between 1,000,000 and 1,500,000; and 0.650 mg magnesium stearate.

6. A solid dosage form in tablet or pellet form, for oral administration of roflumilast, comprising 0.25 mg of roflumilast; from 40 to 99% by weight, based on the finished dosage form of one or more fillers; from 2 to 35% by weight, based on the finished dosage form of one or more disintegrants; polyvinylpyrrolidone having a weight average molecular weight of between 1,000,000 and 1,500,000; and a lubricant and wherein said dosage form provides immediate release of said roflumilast.

7. A solid dosage form in tablet or pellet form, for oral administration of roflumilast, comprising 0.5 mg of roflumilast; from 40 to 99% by weight, based on the finished dosage form of one or more fillers; from 2 to 35% by weight, based on the finished dosage form of one or more disintegrants; polyvinylpyrrolidone having a weight average molecular weight of between 1,000,000 and 1,500,000; and a lubricant and wherein said dosage form provides immediate release of said roflumilast.

8. A solid dosage form in tablet or pellet form, for oral administration of roflumilast, comprising 0.5 mg of roflumilast; from 40 to 99% by weight, based on the finished dosage form of one or more fillers; from 2 to 35% by weight, based on the finished dosage form of one or more disintegrants; polyvinylpyrrolidone; and a lubricant, and wherein said dosage form provides immediate release of said roflumilast.

9. The solid dosage form of claim 8, wherein said polyvinylpyrrolidone is selected from the group consisting of polyvinylpyrrolidone having a weight average molecular weight of between 28,000 and 34,000; polyvinylpyrrolidone having a weight average molecular weight of between 44,000 and 54,000; and polyvinylpyrrolidone having a weight average molecular weight of between 1,000,000 and 1,500,000.

10. The dosage form according to claim 7, wherein the proportion of polyvinylpyrrolidone is from 1 to 5% by weight, based on the finished dosage form.

11. The dosage form according to claim 10, wherein the proportion of polyvinylpyrrolidone is from 2 to 3% by weight, based on the finished dosage form.

12. The dosage form according to claim 10, wherein the proportion of polyvinylpyrrolidone is from 1.98 to 3% by weight, based on the finished dosage form.

13. The dosage form according to claim 7, wherein the filler is selected from the group consisting of sugar alcohols, starches, saccharides and mixtures thereof.

14. The dosage form according to claim 7, wherein the filler is selected from the group consisting of corn starch, microcrystalline cellulose, lactose and mixtures thereof.

15. The dosage form according to claim 7, wherein the filler includes corn starch and lactose.

16. The dosage form according to claim 7, wherein the lubricant is selected from the group consisting of sodium stearyl fumarate, magnesium stearate, calcium stearate, stearic acid, talc and colloidal anhydrous silica.

17. The dosage form according to claim 16, wherein the lubricant is magnesium stearate.

18. The dosage form according to claim 8, wherein the proportion of polyvinylpyrrolidone is from 1 to 5% by weight, based on the finished dosage form.

19. The dosage form according to claim 18, wherein the proportion of polyvinylpyrrolidone is from 2 to 3% by weight, based on the finished dosage form.

20. The dosage form according to claim 19, wherein the proportion of polyvinylpyrrolidone is from 1.98 to 3% by weight, based on the finished dosage form.

21. The dosage form according to claim 8, wherein the filler is selected from the group consisting of sugar alcohols, starches, saccharides and mixtures thereof.

22. The dosage form according to claim 8, wherein the filler is selected from the group consisting of corn starch, microcrystalline cellulose, lactose and mixtures thereof.

23. The dosage form according to claim 8, wherein the filler includes corn starch and lactose.

24. The dosage form according to claim 8, wherein the lubricant is selected from the group consisting of sodium stearyl fumarate, magnesium stearate, calcium stearate, stearic acid, talc and colloidal anhydrous silica.

25. The dosage form according to claim 24, wherein the lubricant is magnesium stearate.

26. The dosage form according to claim 9, wherein the proportion of polyvinylpyrrolidone is from 1 to 5% by weight, based on the finished dosage form.

27. The dosage form according to claim 26, wherein the proportion of polyvinylpyrrolidone is from 2 to 3% by weight, based on the finished dosage form.

28. The dosage form according to claim 27, wherein the proportion of polyvinylpyrrolidone is from 1.98 to 3% by weight, based on the finished dosage form.

29. The dosage form according to claim 9, wherein the filler is selected from the group consisting of sugar alcohols, starches, saccharides and mixtures thereof.

30. The dosage form according to claim 9, wherein the filler is selected from the group consisting of corn starch, microcrystalline cellulose, lactose and mixtures thereof.

31. The dosage form according to claim 9, wherein the filler includes corn starch and lactose.

32. The dosage form according to claim 9, wherein the lubricant is selected from the group consisting of sodium stearyl fumarate, magnesium stearate, calcium stearate, stearic acid, talc and colloidal anhydrous silica.

33. The dosage form according to claim 32, wherein the lubricant is magnesium stearate.

34. The dosage form according to claim 6, wherein the proportion of polyvinylpyrrolidone is from 1 to 5% by weight, based on the finished dosage form.

35. The dosage form according to claim 34, wherein the proportion of polyvinylpyrrolidone is from 2 to 3% by weight, based on the finished dosage form.

36. The dosage form according to claim 34, wherein the proportion of polyvinylpyrrolidone is from 1.98 to 3% by weight, based on the finished dosage form.

37. The dosage form according to claim 6, wherein the filler is selected from the group consisting of sugar alcohols, starches, saccharides and mixtures thereof.

38. The dosage form according to claim 6, wherein the filler is selected from the group consisting of corn starch, microcrystalline cellulose, lactose and mixtures thereof.

39. The dosage form according to claim 6, wherein the filler includes corn starch and lactose.

40. The dosage form according to claim 6, wherein the lubricant is selected from the group consisting of sodium stearyl fumarate, magnesium stearate, calcium stearate, stearic acid, talc and colloidal anhydrous silica.

41. The dosage form according to claim 40, wherein the lubricant is magnesium stearate.

* * * * *